(12) United States Patent
Lee et al.

(10) Patent No.: US 8,846,110 B2
(45) Date of Patent: Sep. 30, 2014

(54) POLYMERIC SYSTEMS FOR THE DELIVERY OF ANTICANCER DRUGS

(75) Inventors: Young B. Lee, Clarksburg, MD (US);
Deog J. Kim, Rockville, MD (US);
Chang H. Ahn, Rockville, MD (US)

(73) Assignee: Rexahn Pharmaceuticals, Inc., Rockville, MD (US)

( * ) Notice: Subject to any disclaimer, the term of this patent is extended or adjusted under 35 U.S.C. 154(b) by 0 days.

(21) Appl. No.: 12/903,927

(22) Filed: Oct. 13, 2010

(65) Prior Publication Data

US 2011/0086111 A1 Apr. 14, 2011

Related U.S. Application Data

(60) Provisional application No. 61/251,156, filed on Oct. 13, 2009.

(51) Int. Cl.

| | | |
|---|---|---|
| A61K 33/24 | (2006.01) | |
| A61K 47/48 | (2006.01) | |
| A61K 45/06 | (2006.01) | |
| A61K 31/337 | (2006.01) | |
| A61K 31/7068 | (2006.01) | |
| C08F 220/60 | (2006.01) | |
| C08F 220/58 | (2006.01) | |

(52) U.S. Cl.
CPC ......... *A61K 31/337* (2013.01); *A61K 47/48176* (2013.01); *A61K 45/06* (2013.01); *A61K 33/24* (2013.01); *A61K 31/7068* (2013.01); *C08F 220/60* (2013.01); *C08F 220/58* (2013.01)
USPC ............ 424/649; 514/49; 514/449; 525/54.1; 525/54.2; 525/328.4; 525/329.4

(58) Field of Classification Search
None
See application file for complete search history.

(56) References Cited

U.S. PATENT DOCUMENTS

| | | |
|---|---|---|
| 3,931,111 A | 1/1976 | Kopecek et al. |
| 3,931,123 A | 1/1976 | Vacik et al. |
| 3,997,660 A | 12/1976 | Kopecek et al. |
| 4,062,831 A | 12/1977 | Kopecek et al. |
| 4,074,039 A | 2/1978 | Lim et al. |
| 4,097,470 A | 6/1978 | Drobnik et al. |
| 5,037,883 A | 8/1991 | Kopecek et al. |
| 5,258,453 A | 11/1993 | Kopecek et al. |
| 5,965,118 A | 10/1999 | Duncan et al. |
| 6,342,221 B1 | 1/2002 | Thorpe et al. |
| 6,346,349 B1 | 2/2002 | Briscoe et al. |
| 6,348,209 B2 | 2/2002 | Placke et al. |
| 6,692,734 B2 | 2/2004 | Stewart et al. |
| 7,166,733 B2 | 1/2007 | Nowotnik et al. |
| 2001/0038830 A1 | 11/2001 | Stewart et al. |
| 2001/0041189 A1 | 11/2001 | Xu |
| 2002/0077279 A1 | 6/2002 | Kumar et al. |
| 2002/0103259 A1 | 8/2002 | Martinez et al. |
| 2004/0234497 A1 | 11/2004 | Luo et al. |
| 2005/0013818 A1 | 1/2005 | Karin et al. |
| 2005/0129769 A1 * | 6/2005 | Barry et al. ................... 424/486 |
| 2005/0287114 A1 | 12/2005 | Wang et al. |
| 2006/0014695 A1 | 1/2006 | Ghandehari et al. |
| 2006/0269479 A1 | 11/2006 | Colton et al. |
| 2007/0287680 A1 | 12/2007 | Cuchelkar et al. |
| 2008/0193377 A1 | 8/2008 | Line et al. |
| 2009/0104143 A1 | 4/2009 | Luo et al. |

FOREIGN PATENT DOCUMENTS

| | | |
|---|---|---|
| FR | 2 858 936 A1 | 2/2005 |
| JP | S61-243026 A | 10/1986 |
| JP | 2003-511423 A | 3/2003 |
| JP | 2005-535604 A | 11/2005 |
| JP | 2008-515915 A | 5/2008 |
| WO | WO-0066091 A1 | 11/2000 |
| WO | WO-02/07770 A2 | 1/2002 |
| WO | WO-2006/042146 A2 | 4/2006 |
| WO | WO-2006113666 A2 | 10/2006 |
| WO | WO-2007067417 A1 | 6/2007 |
| WO | WO-2008/034391 A1 | 3/2008 |
| WO | WO-2008/076771 A2 | 6/2008 |

OTHER PUBLICATIONS

Duncan R, P Kopeckova, J Strohalm, IC Hume, JB Lloyd, and J Kopecek. 1988. Anticancer agents coupled to N-(2-hydroxypropyl)methacrylamide copolymers. II. Evaluation of daunomycin conjugates in vivo against L1210 leukaemia. Br. J. Cancer; 57: 147-156.*
Lyseng-Williamson KA, and C Fenton. 2005. Docetaxel: A review of its use in metastatic breast cancer. Drugs; 65(17): abstract.*
Arap et al., Science, vol. 279, pp. 377-380, 1998.
Borgman et al., Journal of Controlled Release, vol. 132, pp. 193-199, 2008.
Capello et al., Journal of Nuclear Medicine, vol. 45, pp. 1716-1720, 2004.
Cavallaro, G. et al., "Folate-mediated targeting of polymeric conjugates of gemcitabine", International Journal of Pharmaceutics, Elsevier BV, NL, vol. 307, No. 2, Jan. 13, 2006, pp. 258-269.
Choi et al., Journal of Bioactive and Compatible Polymers, vol. 14, pp. 447-456, 1999.
Christie et al., Advanced Drug Delivery Reviews, vol. 55, pp. 421-437, 2003.
Duncan et al., Biochimica et Biophysica Acta, vol. 880, pp. 62-71, 1986.
Duncan et al., Human and Experimental Toxicology, vol. 17, pp. 93-104, 1998.

(Continued)

*Primary Examiner* — Carlos Azpuru
*Assistant Examiner* — David Browe
(74) *Attorney, Agent, or Firm* — Venable LLP; Keith G. Haddaway; Lars H. Genieser

(57) ABSTRACT

The present invention relates to compositions for the treatment of cancerous tissues in warm-blooded animals containing one or two anticancer agents attached to polymeric carriers having monomer units derived from one or more of N-(2-carboxypropyl)methacrylamide (2-CPMA), N-(3-carboxypropyl)methacrylamide (3-CPMA), N-(2-aminopropyl)methacrylamide (2-APMA) and/or N-(3-aminopropyl)methacrylamide (3-APMA) are also included. Anticancer agents in compositions can be attached to said polymeric carrier by side-chains which can be susceptible to hydrolysis by lysosomal enzymes intracellularly. Compositions can also include a targeting ligand attached to the polymeric carrier, optionally through a second linker.

20 Claims, 4 Drawing Sheets

(56) References Cited

OTHER PUBLICATIONS

Etrych, T. et al., "Synthesis of HPMA Copolymers Containing Doxorubicin Bound via a Hydrazone Linkage. Effect of Spacer on Drug Release and in vitro Cytotoxicity", Macromolecular Bioscience, Viley Vch Verlag, Veinheim, DE, vol. 2, No. 1, Jan. 1, 2002, pp. 43-52.

Felding-Habermann et al., Clinical and Experimental Metastasis, vol. 19, pp. 427-436, 2002.

International Search Report and Written Opinion for International Application No. PCT/US2009/059869, Dated Apr. 7, 2010.

Koivunen et al., Biotechnology, vol. 13, pp. 265-270, 1995.

Kopecek et al., Annals of the New York Academy of Science, vol. 446, pp. 93-104, 1985.

Kopecek et al., European Polymer Journal, vol. 9, pp. 7-14, 1973.

Kopecek, J. et al., "HPMA copolymer-anticancer drug conjugates: design, activity, and mechanism of action", European Journal of Pharmaceutics and Biopharmaceutics, Elsevier Science Publishers B.V., Amsterdam, NL, vol. 50, No. 1, Jul. 3, 2000, pp. 61-81.

Lammers, T. et al., "Image-guided and passively tumour-targeted polymeric nanomedicines for radiochemotherapy", British Journal of Cancer, vol. 99, Sep. 2, 2008, pp. 900-910.

Lu et al., Advanced Drug Delivery Reviews, vol. 54, pp. 675-693, 2002.

Mitra et al., Journal of Controlled Release, vol. 102, pp. 191-201, 2005.

Mitra, A. et al., "Polymeric conjugates of mono- and bi-cyclic alphaVbeta3 binding peptides from tumor targeting", Journal of controlled Release, Elsevier, Amsterdam, NL, vol. 114, No. 2, Aug. 28, 2006, pp. 175-183.

Pasut, G. et al., "Antitumoral activity of PEG-gemcitabine prodrugs targeted by folic acid", Journal of Controlled Release, Elsevier, Amsterdam, NL, vol. 127, No. 3, May 8, 2008, pp. 239-248.

Putnam et al., Advances in Polymer Science, vol. 122 (Biopolymers II), pp. 55-123, 1995.

Skehan et al., Journal of the National Cancer Institute, vol. 82, pp. 1107-1112, 1990.

U.S. Appl. No. 60/732,633, part of International Application No. PCT/US2006/014483, published as WO 2006/113666 on Oct. 26, 2006.

Office Action issued by the USPTO in U.S. Appl. No. 12/575,276 on Jun. 19, 2012.

Sampath et al., "Interstitial Docetaxel (Taxotere®): a Novel Treatment for Experimental Malignant Glioma," Journal of Neurooncology, vol. 80, No. 1, pp. 9-17, 2006.

Lokich et al. "Alternating Doublets: Establishing the Optimal Multifractionated Dosing Schedule to Administer Docetaxel, Cisplatin, Gemcitabine, and Vinorelbine in Combination," Cancer Investigation, vol. 21, No. 6, pp. 830-836, 2003.

International Preliminary Report on Patentability issued in International Application No. PCT/US2009/059869 dated Apr. 12, 2011.

International Preliminary Report on Patentability issued in International Application No. PCT/US2010/052510 dated Apr. 17, 2012.

Office Action issued in European Application No. 09793342.8 dated Oct. 9, 2012.

English translation of Office Action issued in Chinese Application No. 200980148874.9 dated Aug. 23, 2012.

Drug Bank, "Docetaxel," Accessed: Dec. 19, 2002, pp. 1-8, URL: http://www.drugbank.ca/drugs/DB01248.

IPCS INCHEM, "Cisplatin," Accessed Dec. 19, 2012, pp. 1-43, URL: http://www.inchem.org/documents/pims/pharm/cisplat.htm.

Lammers et al., "Simultaneous delivery of doxorubicin and gemcitabine to tumors in vivo using prototypic polymeric drug carriers," Biomaterials 30: 3466-3475 (2009)).

Office Action issued in Australian Patent Application No. 2009302387 dated Jan. 20, 2014.

Office Action issued in Chinese Patent Application No. 200980148874.9 dated Aug. 29, 2013.

Office Action issued in Chinese Patent Application No. 201080055030.2 dated Apr. 26, 2013.

Office Action issued in Chinese Patent Application No. 201080055030.2 dated Mar. 7, 2014.

Office Action issued in Japanese Patent Application No. 2011-531149 dated Oct. 1, 2013.

Office Action issued in U.S. Appl. No. 12/575,276 dated Nov. 29, 2013.

Park et al., "Biodegradable Polymers for Microencapsulation of Drugs," Molecules 2005, 10, 146-161.

Andoulakis et al., "Treatment of Pancreatic Cancer with Docetaxel and Granulocyte Colony-Stimulating Factor: A Multicenter Phase II Study", J. Clin. Oncol., 17(6) (Jun. 1999) 1779-1785.

Bedikian et al., "Phase II Trial of Docetaxel in Patients With Advanced Cutaneous Malignant Melanoma Previously Untreated With Chemotherapy", J. Clin. Oncol., 13(12) (Dec. 1995) 2895-2899.

Coleman et al., "Phase II study of docetaxel in patients with liver metastases from breast cancer", Annals Oncol., 11 (2000) 541-546.

Kaye et al., "Phase II Trials of Docetaxel (Taxotere®) in Advanced Ovarian Cancer—an Updated Overview", Eur. J. Cancer, 33(13) (1997) 2167-2170.

Marur et al., "Phase II Trial of Capecitabine and Weekly Docetaxel in Metastatic Renal Cell Carcinoma", Urol., 72(4) (Oct. 2008).

McKiernan et al., "Phase I Trial of Intravesical Docetaxel in the Management of Superficial Bladder Cancer Refractory to Standard Intravesical Therapy", J. Clin. Oncol., 24(19) (Jul. 1, 2006) 3075-3080.

Okuno et al., "Small Cell Lung Cancer: Current Therapy and Promising New Regimens", Oncologist, 7 (2002) 234-238.

Rigas et al., "Docetaxel in the Treatment of Esophageal Cancer", Seminars Oncol., 32 (suppl. 4) (2005) S39-S51.

Takekida et al., "Phase II Study of Combination Chemotherapy With Docetaxel and Carboplatin for Locally Advanced or Recurrent Cervical Cancer", Int'l J. Gynecol. Cancer, 20(9) (Dec. 2010) 1563-1568.

Wikipedia, N-(2-Hydroxypropyl) methacrylamide, Accessed: Dec. 20, 2012, pp. 1-2, URL: http://en.wikipedia.org/wiki/N-(2-Hydroxypropyl)_methacrylamide.

International Search Report and Written Opinion for International Application No. PCT/US2010/052510, dated Jun. 23, 2011.

Office Action issued in U.S. Appl. No. 12/575,276 dated Nov. 28, 2012.

Sigma Aldrich Amino Acids Reference Chart, web page on Jul. 8, 2013.

Office Action in U.S. Appl. No. 12/575,276 mailed Jul. 15, 2013.

\* cited by examiner

SEQUENCE LISTING

```
<160> NUMBER OF SEQ ID NOS: 11

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Leu Gly
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Phe Phe Leu
1
```

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Leu Leu Gly
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Phe Tyr Ala
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Phe Gly Phe
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Gly Val Phe
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Phe Phe Gly
1

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 8

Gly Phe Leu Gly Phe
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Phe Leu Gly Phe
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Pro Asp Thr Arg Pro
1               5

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Cys Ala Arg Glu Pro Pro Thr Arg Thr Phe Ala Tyr Trp Gly
1               5                   10                  15
```

POLYMERIC SYSTEMS FOR THE DELIVERY OF ANTICANCER DRUGS

CROSS-REFERENCE TO RELATED APPLICATION

This application claims priority to U.S. Provisional Application No. 61/251,156 filed Oct. 13, 2009, the entire contents of which is hereby incorporated by reference.

FIELD OF THE INVENTION

The present invention includes compositions containing one or two anticancer agents attached to polymeric carriers for the treatment of cancerous tissues in warm-blooded animals. The polymeric carriers include functional groups such as the amino group or carboxylic acid group. One or two anticancer agents in compositions may be attached to said polymeric carrier by side-chains which are susceptible to intracellular hydrolysis by lysosomal enzymes and wherein said polymeric carriers optionally contain a targeting ligand.

BACKGROUND OF THE INVENTION

Many low molecular weight drugs used in chemotherapy rapidly enter all types of cells by random diffusion through the cell membrane. This lack of selectivity decreases availability at the desired target cells or tissue and sometimes causes undesirable side effects. Cellular uptake is rapid so that the therapeutic effect is not extended over a period of time. Furthermore, glomerular filtration can rapidly remove the drugs from the bloodstream.

The covalent attachment of low molecular weight bioactive molecules to soluble polymeric carriers both prevents glomerular filtration and promotes cellular absorption by mechanisms other than just simple diffusion.

Synthetic N-(2-hydroxypropyl)methacrylamide (HPMA) copolymer is an example of a biocompatible, water-soluble, inert and neutral drug carrier for in vivo delivery of anticancer therapeutics (See, for example, U.S. Pat. Nos. 4,062,831 and 4,097,470). The conjugation of anticancer drugs to HPMA copolymers results in many advantageous features over small molecular therapeutics, including improved solubility and bioavailability, preferential accumulation of the conjugates in solid tumors or passive tumor targeting due to the enhanced permeability and retention (EPR) effect, reduced systemic toxicity and enhanced therapeutic efficacy, and down-regulation of multi-drug resistance.

There are currently six HPMA copolymer-drug conjugates at various stages of clinical trials and their preparation and compositions are disclosed in several patents. There are currently two polyglutamate-drug conjugates at various stages of clinical trials, and further polymer-drug conjugates including dextran-drug conjugates and PEG-drug conjugates are reported in clinical or preclinical development.

U.S. Pat. No. 5,037,883 issued Aug. 6, 1991, (Kopecek et al.) describes a drug conjugate of an inert polymeric carrier attached through a peptide linkage to bio-active molecules. This patent describes copolymers of N-(2-hydroxypropyl) methacrylamide containing oligopeptide sequences terminated in anticancer drugs (e.g. adriamycin, daunomycin, melphalan) and bound to targeting moieties (e.g. galactosamine, fucosylamine, anti-Thy 1.2 antibodies, anti-Ia antibodies) that are alleged to have a higher therapeutic efficacy compared to the low molecular weight drugs that contain no polymers. In particular a conjugate containing adriamycin as a drug (bound via a Gly-Phe-Leu-Gly oligopeptide sequence) and galactosamine as a targeting ligand is described. U.S. Pat. No. 6,692,734 (Stewart etc., 2004) and U.S. Pat. No. 7,166,733 (Nowotnik, 2007) describe a poly(HPMA)-GFLG-platinum drug. Luo et al. in US 2004/0234497 discloses a cell-targeted polymeric delivery system of poly(HPMA)-GFLG-HA-doxorubicin that was designed based on the specific interaction between hyaluronic acid (HA) and its cell surface receptors overexpressed on cancer cell surface. In US 2006/0014695, Ghandehari et al., also describes compositions and methods for nucleic acid delivery comprising HPMA conjugated to a polyamine. Another issued patent, U.S. Pat. No. 5,258,453 (Kopecek and Krinick, 1993) describes the combination effect of the anticancer agent and photoactivatable drug by poly(HPMA)-GFLG-adriamycin-ce6-secretin. Lammers et al. showed the delivery of two different chemotherapeutic agents (doxorubicin and gemcitabine) to tumors simultaneously using HPMA copolymers (Biomaterials 30: 3466-3475 (2009)).

There remains a need for additional polymer carriers for the delivery of anticancer drugs and the like.

SUMMARY OF THE INVENTION

Embodiments include therapeutic compositions having a first polymer carrier. The first polymer carrier has a first monomer, which is N-(2-carboxypropyl)methacrylamide (2-CPMA), N-(2-carboxypropyl)methacrylamide (3-CPMA), N-(3-aminopropyl)methacrylamide (3-APMA), or N-(2-aminopropyl)methacrylamide (2-APMA). The therapeutic compositions further include a first anticancer agent attached to the first polymer carrier, optionally through a linker; where the first anticancer agent is attached to the first monomer or to another monomer. For example, the polymer carrier may be a homopolymer of 2-CPMA, 3-CPMA, 3-APMA, or 2-APMA where at least some of the monomer units are chemically attached to an anticancer agent.

In some embodiments, the first polymer carrier has a second monomer. In other words, the first polymer carrier is a copolymer. For example, the polymer carrier is a copolymer having 2-CPMA, 3-CPMA, 3-APMA, and/or 2-APMA monomers. In the case of copolymers, at least some of the 2-CPMA, 3-CPMA, 3-APMA, or 2-APMA may be chemically attached to an anticancer agent. In some embodiments, the first anticancer agent is attached to the second monomer, optionally through a linker. For example, in these copolymers, the 2-CPMA, 3-CPMA, 3-APMA, or 2-APMA monomers may be unmodified, and the copolymer includes a monomer other than 2-CPMA, 3-CPMA, 3-APMA, or 2-APMA that is chemically attached to the anticancer agent. In some embodiments, the second monomer is N-(2-hydroxypropyl)methacrylamide (HPMA), an acrylamide, a methacrylamide, an acrylate or a methacrylate. These monomers may be underivatized or derivatized to be chemically attached to, for example, one or more anticancer agents or targeting ligands, or linkers.

In some embodiments, the composition further includes an additional anticancer agent, different from the first anticancer agent. The additional anticancer agent is attached to the first polymer carrier, optionally through a linker. The additional anticancer agent may be attached to the first monomer or to another monomer. In some embodiments, both anticancer agents are attached to the first type of monomer (i.e. 2-CPMA, 3-CPMA, 2-APMA, or 3-APMA), meaning that at least some individual units of the first monomer have been chemically modified with each anticancer agent. In some embodiments, one anticancer agent is attached to the first monomer, while the other is attached to a monomer other than the first monomer. In some embodiments, both anticancer agents are attached to monomers other than the first monomer. In any case, the monomers to which the two anticancer agents are attached may be the same or different.

In some embodiments, the composition further includes a targeting ligand attached to the first polymer carrier, optionally through a linker. As above, the targeting ligand may be attached to the first monomer or to another monomer. As above, the targeting ligand may be attached to the same type of monomer (either the first or another monomer) as the first anticancer agent or the second anticancer agent (if present). In other example, the targeting ligand is attached to a different type of monomer than the first or second anticancer agent. In some embodiments, the targeting ligand may be RGDfK, EPPT1, or folate.

Embodiments include compositions that further include a second polymer carrier and a second anticancer agent and/or a targeting ligand attached to to the second polymer carrier, optionally through a linker. In some embodiments, second polymer carrier is a polymer comprising a monomer selected from N-(2-hydroxypropyl)methacrylamide (HPMA), N-(2-carboxypropyl)methacrylamide (2-CPMA), N-(3-carboxypropyl)methacrylamide (3-CPMA), N-(3-aminopropyl)methacrylamide (3-APMA), and N-(2-aminopropyl)methacrylamide (2-APMA).

In any embodiment, the first anticancer agent may be attached to the first polymer carrier through a linker. Likewise, where there are multiple anticancer agents and/or targeting ligands attached to a polymer carrier, any or all of them may be attached through a linker. In embodiments having at least two anticancer agents attached to one polymer carrier, both are attached by linkers. In embodiments having more than one linker, each linker may be the same or different.

In some embodiments where at least one anticancer agent is attached to the polymer through a linker, one or more or all of the linkers may be susceptible to cleavage by lysosomal enzymes. Examples of linkers susceptible to cleavage by lysosomal enzymes include oligopeptide sequences, oligosaccharide sequences and structures similar to those in nucleic acids. In some embodiments, the linker is an oligopeptide sequence. Examples of oligopeptide sequences include Gly-Gly, Gly-Phe-Gly, Gly-Phe-Phe, Gly-Leu-Gly, Gly-Val-Ala, Gly-Phe-Ala, Gly-Leu-Phe, Gly-Leu-Ala, Ala-Val-Ala, Gly-Phe-Leu-Gly (SEQ ID NO: 1), Gly-Phe-Phe-Leu (SEQ ID NO: 2), Gly-Leu-Leu-Gly (SEQ ID NO: 3), Gly-Phe-Tyr-Ala (SEQ ID NO: 4), Gly-Phe-Gly-Phe (SEQ ID NO: 5), Ala-Gly-Val-Phe (SEQ ID NO: 6), Gly-Phe-Phe-Gly (SEQ ID NO: 7), Gly-Phe-Leu-Gly-Phe (SEQ ID NO: 8), or Gly-Gly-Phe-Leu-Gly-Phe (SEQ ID NO: 9). In some embodiments, the oligopeptide linker is Gly-Phe-Leu-Gly (SEQ ID NO: 1). In embodiments having more than one linker, a second linker may be an amino acid or peptide. In some embodiments, the second linker may be Gly-Gly (GG).

In some embodiments, the first anticancer agent may be docetaxel, gemcitabine, cisplatin, derivatives of docetaxel, derivatives of gemcitabine, or derivative of cisplatin. In embodiments having at least two anticancer agents, at least one of the anticancer agents may be docetaxel, gemcitabine, cisplatin, a derivative of docetaxel, a derivative of gemcitabine, or a derivative of cisplatin. In some embodiments having at least two anticancer agents, one may be docetaxel, or a derivative of docetaxel, and the other may be gemcitabine or a derivative of gemcitabine. In some embodiments, having two anticancer agents, the first anticancer agent is docetaxel or a derivative of docetaxel, and the second or additional anticancer agent is cisplatin or a derivative of cisplatin.

Embodiments include pharmaceutical compositions including one or more of the above described compositions. Other embodiments include methods of treating neoplastic diseases by administering a therapeutically effective amount of one of the above described compositions. Other embodiments include the use of one of the above described compositions to treat a neoplastic disease.

Compositions according to the invention can include the monomer, N-2-carboxypropyl methacrylamide (2-CPMA) or N-3-carboxypropyl methacrylamide (3-CPMA) which have a carboxylic acid group rather than the neutral hydroxyl group as in HPMA. The CPMA monomers 2-CPMA and 3-CPMA are used to synthesize CPMA based copolymers for the delivery of anticancer agents. The carboxylic acid group has advantages over HPMA in that it can be used for the production of esters, acid halides, acid amides, and acid anhydrides. In addition, the carboxylic acid in this acidic drug carrier can be used for the conjugation of peptides, drugs, or polymers containing other functional group to this carboxylic group. It can be used before polymerization or after polymerization to extend or add the polymeric chains.

Embodiments of the invention include acidic drug carriers, such as 2-CPMA-containing or 3-CPMA-containing polymers and copolymers, and basic drug carriers, such as N2-APMA-containing or 3-APMA-containing polymers and copolymers that are useful polymeric systems for the delivery of one kind of anticancer agent or two kinds of different anticancer agents.

Embodiments of the invention also relate to new polymeric systems to deliver anticancer agents for the treatment of neoplastic diseases. The systems are composed of a water-soluble polymer with one or two different anticancer agents attached to the polymer backbone, for example, through peptide linkages.

Embodiments of the invention relate to conjugates of anticancer agents and/or targeting ligands to water-soluble polymers, such as poly N-(2-carboxypropyl)methacrylamide (p2-CPMA), poly N-(3-carboxypropyl)methacrylamide (p3-CPMA), poly N-(3-aminopropyl)methacrylamide (p3-APMA), or poly N-(2-aminopropyl)methacrylamide) (p2-APMA) and use of those conjugates as specific intracellular carriers of anticancer agents into tumors. Examples of targeting ligands include RGDfK, EPPT1 peptide, or folate.

Embodiments of the present invention include soluble bioactive polymers such as poly N-(2-carboxypropyl)methacrylamide (p2-CPMA), poly N-(3-carboxypropyl)methacrylamide (p3-CPMA), poly N-(3-aminopropyl)methacrylamide (p3-APMA) and poly N-(2-aminopropyl)methacrylamide (p2-APMA) and related copolymers containing the same monomers and having pendant anticancer agents and a pendant targeting ligand attached by enzymatically degradable bonds.

The present invention also provides a method for the treatment of neoplastic diseases by the administration of soluble bioactive copolymers, such as poly N-(2-carboxypropyl)methacrylamide (p2-CPMA), poly N-(3-carboxypropyl)methacrylamide (p3-CPMA), poly N-(2-aminopropyl)methacrylamide (p2-APMA) or poly N-(3-aminopropyl)methacrylamide (p3-APMA) and related copolymers containing the same monomers and containing pendant anticancer agents, optionally attached via enzymatically degradable bonds. The copolymer may also contain a targeting ligand specific for a tumor marker on the cancer cell.

The invention further provides a method for the treatment of neoplastic disease by administration of copolymers containing two or more different anticancer agents.

BRIEF DESCRIPTION OF THE DRAWINGS

FIG. 2 shows schematic representations of example embodiments.

DETAILED DESCRIPTION OF THE INVENTION

Figure 1:
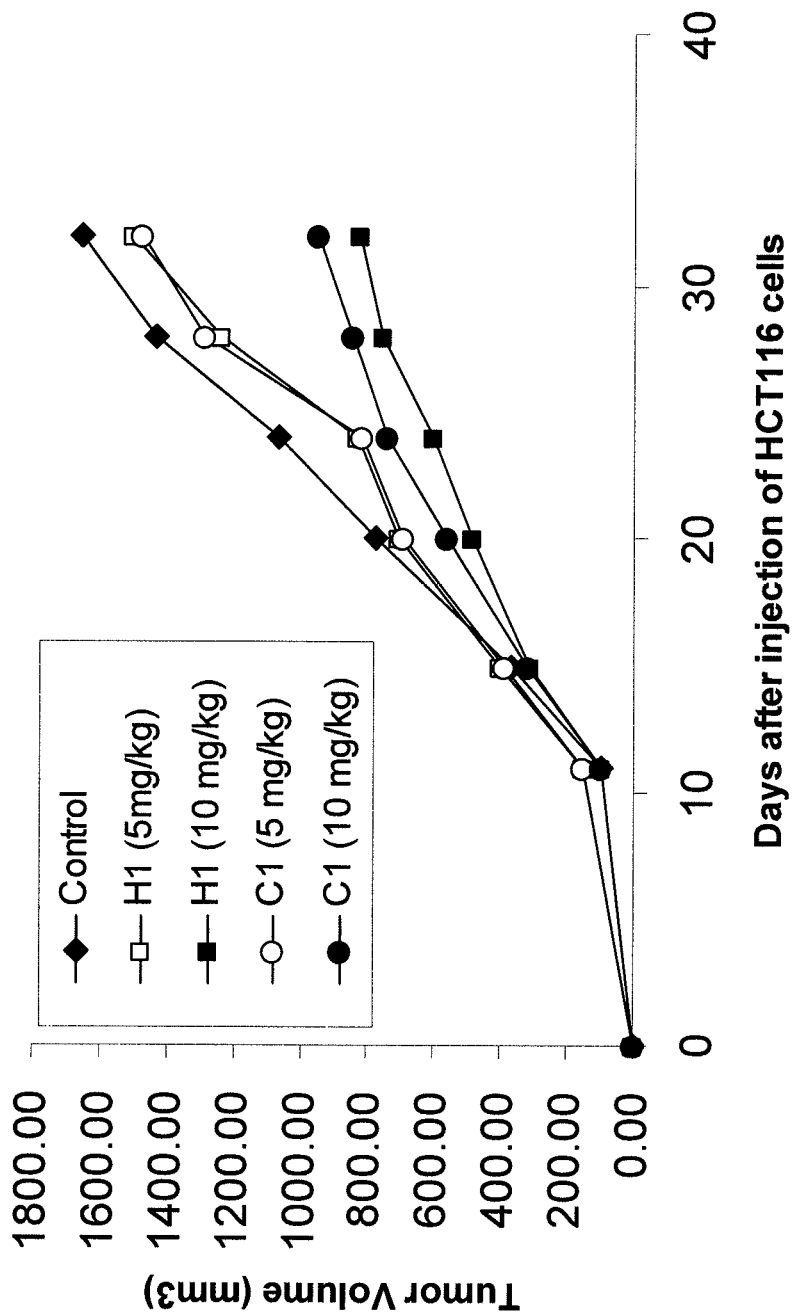
FIG. 1 is a graph showing the inhibition of tumor growth in nude mice subcutaneously injected with HCT116 human colon carcinoma cells by pHPMA-GFLG-Docetaxel (H1) and p2-CPMA-GFLG-Docetaxel (C1). 'GFLG' is disclosed as SEQ ID NO: 1.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are incorporated by reference as if each had been individually incorporated.

Free anticancer drugs diffuse throughout a cell and are not concentrated at a specific subcellular location. In addition, if such drugs are administered intravenously they are systemically distributed to all tissues of the body. The action of these drugs at these unintended distribution sites results in observable systemic side effects. It is thus preferred to localize the drug to the sites in the body where the action is desired. Targeting these agents to the subcellular site where they are most effective increases their efficacy and decreases their toxicity.

Targeting of anticancer drugs to tumors can be achieved by "passive targeting" and "active targeting". Passive targeting involves the use of generally non-specific methods to selectively increase drug deliver to target cells. For example, passive targeting can be achieved by incorporation or attachment of anticancer drugs into macromolecular carriers such as water-soluble polymers. Active targeting utilizes moieties that are specific to recognition molecules (receptors) on the surface of target cells. For example, active targeting can be achieved by attaching cellular targeting moieties to delivery systems such as a macromolecular carrier.

Polymers localize preferentially in solid tumors when compared to normal tissue. This occurs due to a phenomenon called the Enhanced Permeability and Retention ("EPR") effect, which is attributed to morphological changes in tumor tissue or cells, where the leaky vasculature produced due to neoangiogenesis results in the leakage of vascular contents into the extracellular tissue. In addition, the lymphatics may be blocked, which results in the accumulation of macromolecular agents in the extracellular tissue surrounding tumor cells. This phenomenon can be used to target tumor cells by attaching drugs to the polymers. Since polymers localize around tumor cells, the drugs attached to the polymers are also available at higher concentrations around the tumor. Anticancer agents attached to polymers are taken inside cells by endocytosis. Anticancer agents attached to polymers may retain their anticancer activity. However, since the agents remain covalently attached to the polymer backbone, in some instances they may not be as effective as free agents. This may be overcome by the use of biodegradable or hydrolysable bonds or linkers, such as peptide sequences, to attach the drug to the polymer backbone. When peptide sequences are used, the sequences are chosen such that they can be degraded inside the cell under specific conditions.

In addition, cancer cells often have surface molecules that are either absent in normal tissue or over-expressed in comparison to the normal tissue. These may include growth factor receptors and/or certain antigens. Attaching recognition molecules to polymers that bind to these molecules results in selective binding of the carrier to tumor cells and tissue and a high concentration of polymers in the local environment of the tumor. Such targeting moieties include antibodies and peptidyl ligands for cell surface receptors. Receptor mediated endocytosis initiated by the binding of some of these recognition molecules to their receptors may result in an increased intracellular concentration and correspondingly may result in an enhanced therapeutic effect.

Polymer-based therapeutics have a large hydrodynamic volume, which translates into a longer intravascular half-life. Polymer-based therapeutics also enhance the solubility and the bioavailability of insoluble drugs. Other advantages afforded by polymer-based therapeutics include increased maximum tolerated dose, decreased non-specific toxicity, enhanced induction of apoptosis, and activation of alternate signaling pathways (Kopecek et al., Advances in Polymer Science, 122 (Biopolymers II): 55-123 (1995)).

Embodiments include new polymer based therapeutics and their use for the treatment of neoplastic diseases. Embodiments include homopolymers and copolymers produced from the polymerization of one or more of N-(2-hydroxypropyl)methacrylamide (HPMA), N-(2-carboxypropyl)methacrylamide (2-CPMA), N-(3-carboxypropyl)methacrylamide (3-CPMA), N-(2-aminopropyl)methacrylamide (2-APMA), or N-(3-aminopropyl)methacrylamide (3-APMA), where the homopolymer or copolymers includes at least one of 2-CPMA, 3-CPMA, 2-APMA, or 3-APMA.

Monomers

As used herein, the terms monomer or comonomer may be used to mean a monomer prior to polymerization. However, the when used in reference to a formed polymer, the terms monomer, comonomer, monomer unit, or comonomer unit refer to the subunit in a polymer or copolymer chain derived from a monomer or comonomer in its un-polymerized form. The use of these terms will be evident to persons skilled in the art in the context of the specification and claims.

As used herein, the terms "HPMA", "2-CPMA", "3-CPMA", "2-APMA" and "3-APMA" mean the compounds N-(2-hydroxypropyl) methacrylamide, N-(2-carboxypropyl) methacrylamide, N-(3-carboxypropyl)methacrylamide (3-CPMA), N-(2-aminopropyl)methacrylamide, and N-(3-aminopropyl)methacrylamide, respectively as represented by the following structure:

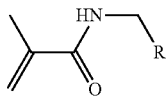

HPMA: R = CH(OH)CH$_3$
2-CPMA: R = CH(COOH)CH$_3$
3-CPMA: R = CH$_2$CH$_2$COOH
2-APMA: R = CH(NH$_2$)CH$_3$
3-APMA: R = CH$_2$CH$_2$NH$_2$

As used herein, an "underivatized" monomer is a monomer that has not been chemically modified. Underivatized monomers include, for example, 2-CPMA, 3-CPMA, HPMA, 2-APMA, 3-APMA, acrylamide, methacrylamide, acryloyl chloride, methacryloyl chloride, acrylates, methacrylates, and other vinylic comonomers. A "derivatized" monomer means a monomer that has been chemically modified (other than by polymerization). The chemical modification may occur before or after polymerization. In some embodiments, a "derivatized" monomer is synthesized before polymerization. In some embodiments, a monomer or monomer unit is "derivatized" after polymerization. A monomer can be "derivatized" to attach, for example, an anticancer agent, a linker, a targeting ligand, a linker-anticancer agent combination, or a linker-targeting ligand combination. Examples of derivatized monomers include 2-CPMA or 3-CPMA, where the carboxylic acid functional group is modified to be directly attached, for example, by a covalent bond, to a linker, anticancer agent or targeting ligand or 2-APMA or 3-APMA, where the amine functional group is modified to be directly attached, for example, by a covalent bond, to a linker, anticancer agent or targeting ligand. Other examples include 2-CPMA or 3-CPMA where the carboxylic acid functional group is directly attached, for example, by a covalent bond, to a linker, where an anticancer agent or targeting ligand is directly attached, for example, by a covalent bond, to the linker. Other examples include 2-APMA or 3- APMA where the amine functional group is directly attached, for example, by a covalent bond, to a linker, where an anticancer agent or targeting ligand is directly attached, for example, by a covalent bond, to the linker.

Polymer-Based Therapeutics

Embodiments of the invention include polymer based therapeutic compounds that can be used, for example, in anticancer therapies. These compounds may increase or alter the targeted delivery of anticancer compounds or other therapeutic compounds. Polymer based therapeutic compounds include homopolymers and copolymers produced from the polymerization of one or more of N-(2-hydroxypropoyl) methacrylamide (HPMA), N-(2-carboxypropyl)methacrylamide (2-CPMA), N-(3-carboxypropyl)methacrylamide (3-CPMA), N-(2-aminopropyl)methacrylamide (2-APMA), or N-(3-aminopropyl)methacrylamide (3-APMA), where the homopolymer or copolymers includes at least one of 2-CPMA, 3-CPMA, 2-APMA, or 3-APMA, and where the homopolymer or copolymer includes at least one anticancer agent.

These polymer based therapeutic compounds comprise an anticancer agent and a polymer carrier. The polymer based therapeutic compounds may optionally comprise a linker, such as, for example, Gly-Phe-Leu-Gly (SEQ ID NO: 1), and/or a targeting ligand such as, for example, RGDfK, EPPT1 peptide or folate. As used herein, a polymer carrier is the polymer backbone attached to one or more anticancer agents, linkers, targeting ligands, linker-anticancer agent combinations, or linker-targeting ligand combinations.

Embodiments include therapeutic compositions having a first polymer carrier. The first polymer carrier has a first monomer, which is either N-(2-carboxypropyl)methacrylamide (2-CPMA), N-(3-carboxypropyl)methacrylamide (3-CPMA), N-(3-aminopropyl)methacrylamide (3-APMA), or N-(2-aminopropyl)methacrylamide (2-APMA). The therapeutic compositions further include a first anticancer agent attached to the first polymer carrier, optionally through a linker; where the first anticancer agent is attached to the first monomer or to another monomer. For example, the polymer carrier may be a homopolymer of 2-CPMA, 3-CPMA, 3-APMA, or 2-APMA where at least some of the monomer units are chemically attached to an anticancer agent.

In some embodiments, the first polymer carrier has a second monomer. In other words, the first polymer carrier is a copolymer, i.e., a copolymer having 2-CPMA, 3-CPMA, 3-APMA, and/or 2-APMA monomers. In the case of copolymers, at least some of the 2-CPMA, 3-CPMA, 3-APMA, or 2-APMA monomer units may be chemically attached to an anticancer agent. In some embodiments, the first anticancer agent is attached to a second monomer, optionally through a linker. For example, in some copolymers, the 2-CPMA, 3-CPMA, 3-APMA, or 2-APMA monomers may be unmodified, and the copolymer includes a monomer other than 2-CPMA, 3-CPMA, 3-APMA, or 2-APMA that is chemically attached to the anticancer agent. In some embodiments, the second monomer is N-(2-hydroxypropyl)methacrylamide (HPMA), an acrylamide, a methacrylamide, an acrylate or a methacrylate. These monomers may be underivatized or derivatized to be chemically attached to, for example, one or more anticancer agents or targeting ligands, or linkers. Comonomers used in HPMA polymer and copolymer delivery systems known in the art are example comonomers for use in the present invention.

In some embodiments, the composition further includes an additional anticancer agent, different from the first anticancer agent. The additional anticancer agent is attached to the first polymer carrier, optionally through a linker. The additional anticancer agent may be attached to the first monomer or to another monomer. In some embodiments, both anticancer agents are attached to the first monomer, meaning that different units of the first monomer have been chemically modified with each anticancer agent. In such cases, some monomer units are attached to the first anticancer agent, and some to the second anticancer agent, while some are underivatized. In some embodiments, one anticancer agent is attached to the first monomer, while the other is attached to a monomer other than the first monomer. In some embodiments, both anticancer agents are attached to monomers other than the first monomer. In any case, the monomers to which the two anticancer agents are attached may be the same or different.

In some embodiments, the composition further includes a targeting ligand attached to the first polymer carrier, optionally through a linker. As above, the targeting ligand may be attached to the first monomer or to another monomer. As above, the targeting ligand may be attached to the same monomer (either the first or another monomer) as the first anticancer agent, or the second anticancer agent if present. In other words, the monomer attached to the first anticancer agent is of the same type (i.e. 2-CPMA, 3-CPMA, 2-APMA, 3-APMA, HPMA, acrylate, methacrylate, acrylamide, or methacrylamide) as the monomer attached to the targeting ligand. In some embodiments, the targeting ligand is attached or to a different type of monomer than the first anticancer agent. In other words, the monomer unit attached to the targeting ligand is different than the monomer unit attached to the first anticancer agent. The targeting ligand may be, for example, RGDfK, EPPT1, or folate.

In any embodiment, the first anticancer agent may be attached to the first polymer carrier through a linker. Likewise, where there are multiple anticancer agents and/or targeting ligands attached to a polymer carrier, any or all of them may be attached through a linker. In some embodiments having at least two anticancer agents attached to one polymer carrier, both are attached by linkers.

Embodiments include compositions where the first polymer carrier has between about 5% and about 99.7% of underivatized monomer units. In other embodiments, the polymer carrier includes between about 25% and about 98% of underivatized monomer units. In some embodiments, the polymer carrier includes between about 50% and about 98% of underivatized monomer units. In some embodiments, the polymer carrier has more than about 5%, more than about 10%, more than about 20%, more than about 25%, more than about 40%, more than about 50%, more than about 70%, more than about 80%, or more than 90% of underivatized monomer units. In some embodiments, the polymer carrier has less than about 99.5%, less than about 99.0%, less than about 98.0%, or less than about 95% of underivatized monomer units. The underivatized monomer units may be, for example, the first monomer unit (i.e. 2-CPMA, 3-CPMA, 2-APMA, or 3-APMA), or another underivatized monomer unit.

Embodiments include polymers where the first polymer carrier has between about 0.1 mol % and about 20.0 mol % of derivatized monomer units attached to an anticancer agent. In some embodiments, the first polymer carrier has more than about 0.1 mol %, more than about 0.2 mol %, more than about 0.5 mol %, more than about 1.0 mol %, more than about 2.0 mol %, more than about 5.0 mol %, or more than about 7.0 mol % of derivatized monomer units attached to an anticancer agent. In some embodiments the first polymer carrier has less than about 20 mol %, less than about 15 mol %, less than about 10 mol % or less than about 5.0 mol % of derivatized monomer units attached to an anticancer agent.

Embodiments include compositions where the first polymer carrier has between about 0.1 mol % and about 94.8 mol % of derivatized monomer units attached to a targeting ligand. In some embodiments, the first polymer carrier has more than about 0.1 mol %, more than about 0.5 mol %, more than about 1.0 mol %, more than about 2.0 mol %, more than about 5 mol %, more than about 10 mol %, more than about 20 mol %, more than about 40 mol % or more than about 50 mol % of derivatized monomer units attached to a targeting ligand. In some embodiments, the first polymer carrier has less than about 94.8 mol %, less than about 90 mol %, less than about 80 mol %, less than about 70 mol %, less than about 50mol %, less than about 40 mol % or less than about 20 mol % of derivatized monomer units attached to a targeting ligand.

Embodiments include polymer based therapeutic compounds comprising an anticancer agent and a polymer carrier, and optionally a linker molecule and optionally a targeting ligand such as RGDfK, EPPT1 peptide or folate, wherein the anticancer agent, the polymer carrier, linker molecule, and/or targeting ligand, such as RGDfK, EPPT1 peptide or folate are attached to one another via a covalent bond.

Figure 2A:
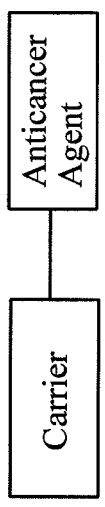
FIG. 2A shows the anticancer agent attached to the polymer carrier via a covalent bond.

There are a number of different ways the anticancer agent, the polymer carrier, the optional linker molecule and the optional targeting ligand can be attached to one another. In some embodiments, the anticancer agent, the polymer carrier, and optionally a linker molecule and optionally a targeting ligand can be directly attached to one another. Example embodiments are described below and shown schematically in FIGS. 2A-2J. For example, the anticancer agent may be attached to the polymer carrier via a covalent bond, as shown in FIG. 2A.

Figure 2B:
FIG. 2B shows a linker molecule directly attached to the polymer carrier via a covalent bond, and the anticancer agent directly attached to the linker molecule via a covalent bond.

In other embodiments, as shown in FIG. 2B, a linker molecule is directly attached to the polymer carrier via a covalent bond, and the anticancer agent is directly attached to the linker molecule via a covalent bond.

Figure 2C:
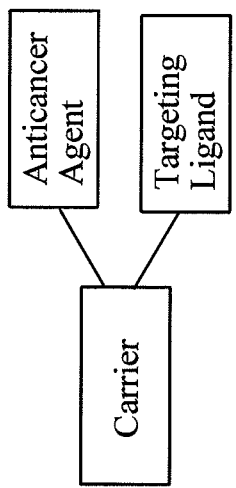
FIG. 2C shows an anticancer agent directly attached to the polymer carrier via a covalent bond, and a targeting ligand directly attached to the polymer carrier via a covalent bond.

In other embodiments, as shown in FIG. 2C, an anticancer agent is directly attached to the polymer carrier via a covalent bond, and a targeting ligand is directly attached to the polymer carrier via a covalent bond.

Figure 2D:
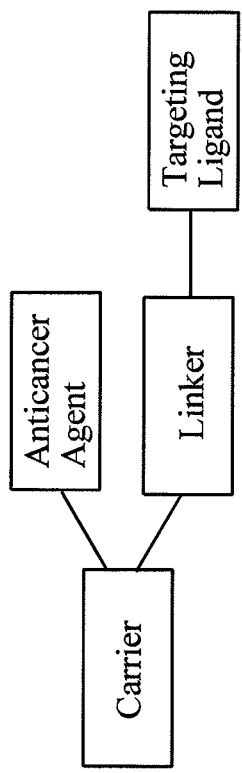
FIG. 2D shows a linker molecule directly attached to the polymer carrier via a covalent bond, and the anticancer agent directly attached to the linker molecule, and a targeting ligand directly attached to the polymer carrier via a covalent bond.

In other embodiments, as shown in FIG. 2D, a linker molecule is directly attached to the polymer carrier via a covalent bond, and the anticancer agent is directly attached to the linker molecule, and a targeting ligand is directly attached to the polymer carrier via a covalent bond.

Figure 2E:
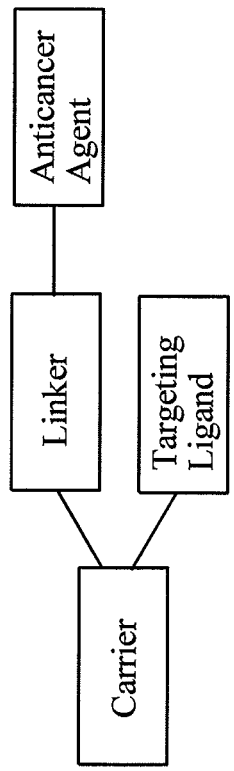
FIG. 2E shows a linker molecule directly attached to the polymer carrier via a covalent bond, and a targeting ligand directly attached to the linker molecule, and an anticancer agent directly attached to the polymer carrier via a covalent bond.

In other embodiments, as shown in FIG. 2E, a linker molecule is directly attached to the polymer carrier via a covalent bond, and a targeting ligand is directly attached to the linker molecule, and an anticancer agent is directly attached to the polymer carrier via a covalent bond.

Figure 2F:
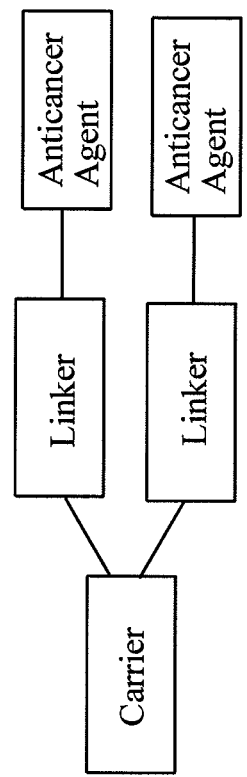
FIG. 2F shows a linker molecule directly attached to the polymer carrier via a covalent bond, and the anticancer agent directly attached to the linker molecule, and a targeting ligand directly attached to a different linker molecule, directly attached to the polymer carrier via a covalent bond.
Figure 2G:
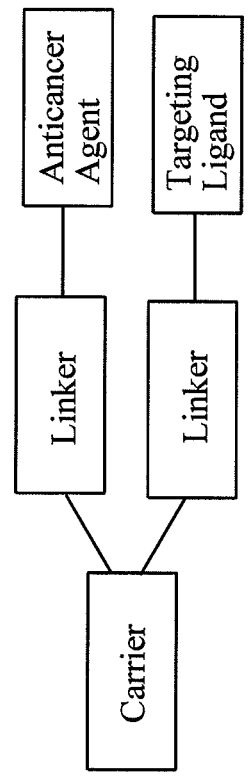
FIG. 2G shows a compound having two anticancer agents, each separated from the carrier by separate linkers.

In other embodiments, as shown in FIG. 2F, a linker molecule is directly attached to the polymer carrier via a covalent bond, and the anticancer agent is directly attached to the linker molecule, and a targeting ligand is directly attached to a different linker molecule, which is directly attached to the polymer carrier via a covalent bond.

In other embodiments, there may be two or more anticancer agents of different types. For example, in any of the previous embodiments, two different anticancer agents may be used. In embodiments having two or more different anticancer agents, the anticancer agents may be attached directly to the carrier or to a linker attached to the carrier. In some embodiments having two or more different anticancer agents, at least one, but not all, of the anticancer agents are attached to a linker, and the linker is directly attached to the carrier. In other embodiments having two or more different anticancer agents, all of the anticancer agents are attached to separate linkers, and the separate linkers are attached directly to the polymer carrier. An illustration, shown in FIG. 2G of a compound having two anticancer agents, each separated from the carrier by separate linkers is shown below. In all cases, the linkers are optional, and may be the same or different.

Figure 2H:
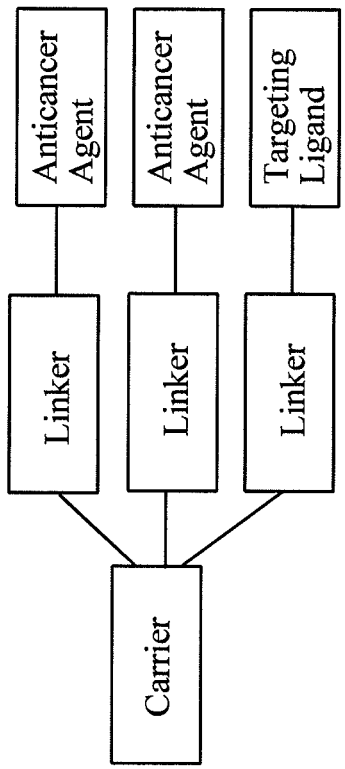
FIG. 2H shows a compound having two anticancer agents with separate linkers, and a targeting ligand, separated by a linker.
Figure 2J:
FIG. 2J shows a polymer carrier having attached thereto a targeting ligand through a linker.
Figure 2G:
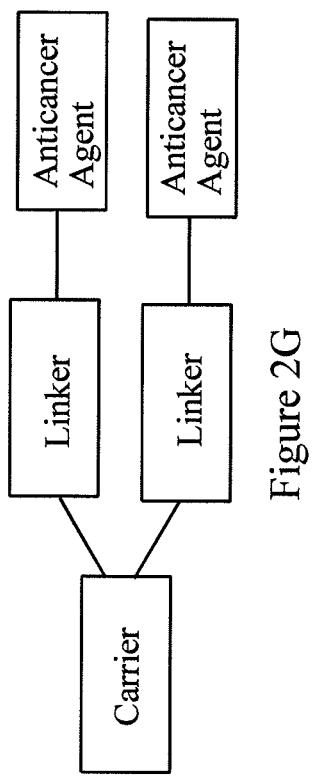
Figure 2I:
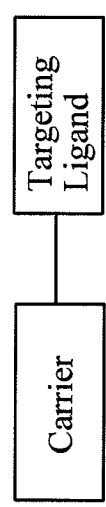
FIG. 2I shows a polymer carrier having attached thereto a targeting ligand.

Embodiments, as shown in FIG. 2H, for example having two or more different anticancer agents may also have a targetting ligand, which is optionally separated from the polymer carrier by a linker. An example of a compound having two anticancer agents with separate linkers, and a targeting ligand, separated by a linker is illustrated below. In all cases, the linkers are optional, and may be the same or different.

In all embodiments using more than one linker, the linkers may be the same or different. For example, where an anticancer agent and a targeting ligand are both separated from the polymer carrier by a linker, the linkers may be the same, or different. Likewise, when two or more anticancer agents are used, and more than one or all are separated from the polymer carrier by linkers, the linkers may be the same, or different.

Embodiments also include compositions and methods that use more than one polymer carrier. For example, a composition may include a first polymer carrier having attached thereto an anticancer agent, optionally through a linker (e.g. FIG. 2A or 2B). The second polymer may also include a targeting ligand (e.g. FIG. 2C, 2D, 2E, or 2F). The composition can also include, for example, a second polymer carrier having attached thereto a targeting ligand, optionally through a linker. (e.g. FIG. 2I or 2J).

In these some embodiments, the second polymer carrier is not limited to polymers having 2-CPMA, 3-CPMA, 3-APMA, or 2-APMA monomers. For example, the second polymer carrier may be a polymer having N-(2-hydroxypropyl)methacrylamide (HPMA), N-(2-carboxypropyl)methacrylamide (2-CPMA), N-(3-carboxypropyl)methacrylamide (3-CPMA), N-(3-aminopropyl)methacrylamide (3-APMA),N-(2-aminopropyl)methacrylamide (2-APMA) or other acrylate and acrylamide monomers. The monomers may be derivatized with an anticancer agent, a linker, a targeting ligand, a linker-anticancer agent combination, or a linker-targeting ligand combination.

In some embodiments, the first and second polymer carriers may be linked together to form a single larger polymer. In such embodiments, the polymers may be linked through any linker capable of attaching to a monomer on each of the polymers. For example, in the first polymer, the linking group may be attached to a monomer that is polymerized to form the first carrier molecule, where the unattached terminus of the linking group has a reactive functional group or leaving group that can be joined to a reactive group on a monomer (or linker) on the second carrier polymer. For example, the first carrier polymer can include a linking group that terminates in a leaving group such as a para-nitrophenoxy (ONp) group. Such a carrier polymer can be reacted with a second carrier molecule that includes an amine group, for example where the second carrier molecule is prepared from 3-APMA. The two carrier polymers can then be linked by displacement of the ONp group by the amine group. In exemplary embodiments of a linked polymer, the linking group is susceptible to cleavage by intracellular hydrolysis or by lysosomal enzymes to release the two separate polymer carriers.

Other compositions can include other combinations of the various delivery systems described above and illustrated in FIGS. 2A-2J. Methods of treatment include coadministration of any of these polymer delivery system combinations.

The anticancer agent, the polymer carrier, the linker molecule and the target ligand used to produce the compounds are discussed below.

1. Anticancer Agent

An "anticancer agent" means any agent useful to combat cancer. Any anticancer agent may be used that can be directly or indirectly attached to the polymer carrier and/or the linker. A partial list of anticancer agents that can be used with the disclosed compositions can be found in, for example, U.S. Pat. No. 5,037,883, which is herein incorporated by reference as well as any publications and patents, or patent applications, cited therein which contain anticancer agents. U.S. Pat. Nos. 6,348,209, 6,346,349, and 6,342,221 also describe agents related to anticancer compounds. Classes of anticancer agents include, but are not limited to, chemotherapeutic agents, cytotoxins, antimetabolites, alkylating agents, protein kinase inhibitors, anthracyclines, antibiotics, antimitotic agents (e.g. antitubulin agents), corticosteroids, radiopharmaceuticals, and proteins (e.g. cytokines, enzymes, or interferons). Anticancer agents include, for example, small molecule organic compounds, macromolecules, metal containing compounds, and compounds or chelates that include radionuclides. In example embodiments, the anticancer compound is a small molecule organic compound. Specific examples include, but are not limited to docetaxel, gemcitabine, imatinib (Gleevec®), 5-fluorouracil, 9-aminocamptothecin, amine-modified geldanamycin, doxorubicin, paclitaxel (Taxol®), cisplatin, procarbazine, hydroxyurea, meso e-chlorin, Gd(+3) compounds, asparaginase, and radionuclides (e.g I-131, Y-90, In-111, and Tc-99m). There are many anticancer agents known in the art and many continue to be developed. In some embodiments, the "anticancer agent" is docetaxel or gemcitabine. Some embodiments include two or more anticancer agents. Some embodiments include two anticancer agents. Some embodiments include docetaxel and gemcitabine.

In some embodiments, the first anticancer agent is docetaxel, gemcitabine, cisplatin, derivatives of docetaxel, derivatives of gemcitabine, or derivatives of cisplatin. In some embodiments having at least a first and second anticancer agent, at least one of the first and second anticancer drug moieties is docetaxel, gemcitabine, cisplatin, derivatives of docetaxel, derivatives of gemcitabine, or derivatives of cisplatin. In other embodiments having a first and second anticancer agent, the first anticancer drug moiety is docetaxel or a derivative thereof and the second anticancer drug moiety is gemcitabine, cisplatin or a derivative thereof.

As will be appreciated, the anticancer agent, as attached to the polymer carrier, is modified compared to the anticancer agent per se. One of ordinary skill will be able to make the necessary chemical modifications of the anticancer agent for attaching the anticancer agent to the polymer carrier or linking molecule based on the description below. Making a chemical modification to attach an anticancer agent produces a "derivative" of that anticancer agent, as used herein. For example, a "derivative" of docetaxel, gemcitabine or cisplatin include chemically modified analogs of docetaxel, gemcitabine or cisplatin that enable attachment of docetaxel, gemcitabine, or cisplatin to the polymer carrier or linker. The derivative should not interfere with the activity of the anticancer agent. In embodiments having a cleavable linker, upon bond cleavage, the anticancer agent, or an active derivative thereof, is released.

2. Polymer Carrier

In one embodiment, the polymer carrier is a polymer produced by the polymerization of an unsaturated monomer. Examples of monomers include, but are not limited to, acrylates and methacrylates, acrylamides, and methacrylamides. In some embodiments of this invention, the polymer carrier is a homopolymer produced from the polymerization of N-(2-carboxypropyl)methacrylamide (2-CPMA), N-(3-carboxypropyl)methacrylamide (3-CPMA), N-(2-aminopropyl)methacrylamide (2-APMA), N-(3-aminopropyl)methacrylamide (3-APMA). In other embodiments, the polymer carrier is a heteropolymer or copolymer produced from the polymerization of two or more comonomer units where at least one monomer unit is N-(2-carboxypropyl)methacrylamide (2-CPMA), N-(3-carboxypropyl)methacrylamide (3-CPMA), N-(2-aminopropyl)methacrylamide (2-APMA), N-(3-aminopropyl)methacrylamide (3-APMA).

As used here, a polymer carrier that is a homopolymer of 2-CPMA, 3-CPMA, 2-APMA, or 3-APMA means that the polymer backbone is derived from 2-CPMA, 3-CPMA, 2-APMA or 3-APMA, but individual monomer units may be attached to, for example, a linker, an anticancer agent, a targeting ligand, a linker attached to an anticancer agent, or a linker attached to a targetting ligand.

A polymer carrier that is a heteropolymer or copolymer means that the polymer backbone is produced from two or more comonomers where at least one comonomer is 2-CPMA, 3-CPMA, 2-APMA, or 3-APMA, but the individual monomer units may be attached to, for example, a linker, an anticancer agent, a targeting ligand, a linker attached to an anticancer agent, or a linker attached to a targetting ligand, as described above. In some embodiments, the 2-CPMA, 3-CPMA, 2-APMA or 3-APMA monomer may be attached to, for example a linker, an anticancer agent, a targeting ligand, a linker attached to an anticancer agent, or a linker attached to a targetting ligand. In some embodiments, a comonomer that is not 2-CPMA, 3-CPMA, 2-APMA or 3-APMA may be attached to, for example, a linker, an anticancer agent, a targeting ligand, a linker attached to an anticancer agent, or a linker attached to a targetting ligand.

The carrier polymer molecule is a large macromolecule of at least 5,000 daltons. The polymer carrier can range from about 5,000, to about 1,000,000 daltons, from about 5,000 daltons to about 100,000 daltons, from about 5,000 to about 25,000 daltons, from about 25,000 to about 100,000 daltons, from about 25,000 daltons to about 1,000,000 daltons, or from 100,000 daltons to 1,000,000 daltons. In embodiments where a first and second polymer carrier are coupled or linked, the result polymer of at least 50,000 daltons, or at least about 100,000 daltons. For example, the resultant polymer can range from 50,000 daltons to about 1,000,000 daltons, 100,000 daltons to about 1,000,000 daltons or 100,000 daltons to about 250,000 daltons. The polymer carrier aids in the transport of an anticancer agent across the cell membrane. Thus, when the anticancer agent is directly or indirectly attached to the polymer carrier it typically crosses a cell membrane better than the anticancer agent alone. Some examples of polymer carriers are also described in U.S. Pat. No. 5,258,453 for "Drug delivery system for the simultaneous delivery of drugs activatable by enzymes and light;" U.S. Pat. No. 5,037,883 for "Synthetic polymeric drugs;" U.S. Pat. No. 4,074,039 for "Hydrophilic N,N-diethyl acrylamide copolymers;" U.S. Pat. No. 4,062,831 for "Copolymers based on N-substituted acrylamides, N-substituted methacrylamides and N,N-disubstituted acrylamides and the method of their manufacturing;" U.S. Pat. No. 3,997,660 for "Soluble hydrophilic polymers and process for producing the same;" U.S. Pat. No. 3,931,123 for "Hydrophilic nitrite copolymers;" and U.S. Pat. No. 3,931,111 for "Soluble hydrophilic polymers and process for processing the same" each of which is individually and specifically herein incorporated by reference in its entirety. These polymers can be modified according to the present invention by incorporation of 2-CPMA, 3-CPMA, 2-APMA or 3-APMA monomers. Alternatively, the polymers mentioned above can be used in combination with polymers according to the present invention, for example, as a second polymer carrier.

3. Linker Molecule

A "linker" refers to a group that spatially separates an anticancer agent or a targeting ligand from the polymeric backbone. The linker can be any sort of entity, such as, without limitation, a poly (ethylene glycol), an amino acid or a poly (amino acid), one end of which is capable of forming a covalent bond with the polymer backbone and the other end of which is capable of forming a covalent bond with drug or a targeting ligand. The linkers may be cleavable so that the anticancer agent can be released, for example, under reducing conditions, oxidizing conditions, or by hydrolysis of an ester, amide, hydrazide, or similar linkage that forms the covalent bond between the linker and the anticancer agent. Additionally, the type of linker may augment the selective cytotoxicity (and thus improve the therapeutic index) aspect by permitting selective release of the anticancer agent inside the cells. The structure of the linker may be tailor-made so as to be stable in the blood stream, yet susceptible to hydrolysis by lysosomal enzymes intracellularly. Oligopeptide sequences, oligosaccharide sequences or structures similar to those in nucleic acids also may be used as points of drug attachment. The linkages or peptide spacers can be any of those mentioned in U.S. Pat. No. 5,037,883, for example, Gly-Gly, Gly-Phe-Gly, Gly-Phe-Phe, Gly-Leu-Gly, Gly-Val-Ala, Gly-Phe-Ala, Gly-Leu-Phe, Gly-Leu-Ala, Ala-Val-Ala, Gly-Phe-Leu-Gly (SEQ ID NO: 1), Gly-Phe-Phe-Leu (SEQ ID NO: 2), Gly-Leu-Leu-Gly (SEQ ID NO: 3), Gly-Phe-Tyr-Ala (SEQ ID NO: 4), Gly-Phe-Gly-Phe (SEQ ID NO: 5), Ala-Gly-Val-Phe (SEQ ID NO: 6), Gly-Phe-Phe-Gly (SEQ ID NO: 7), Gly-Phe-Leu-Gly-Phe (SEQ ID NO: 8), or Gly-Gly-Phe-Leu-Gly-Phe (SEQ ID NO: 9). In some embodiments, the linker is a peptide spacer. In some embodiments, the linker is Gly-Phe-Leu-Gly (SEQ ID NO: 1). This spacer will be repeatedly referred to throughout the specification and claims either as Gly-Phe-Leu-Gly (SEQ ID NO: 1) or GFLG (SEQ ID NO: 1), which terms can be used interchangeably. In some embodiments having at least one linker, the linker is susceptible to cleavage by lysosomal enzymes and the linker can be, for example, oligopeptide sequences, oligosaccharide sequences or structures similar to those in nucleic acids. As used herein, a "structure similar to those in nucleic acids" means an oligonucleotide sequence having a phosphodiester-ribose linkage. These linkages may be cleaved, for example, by phosphodiesterases, DNAses, RNAses, and endonucleases. Examples of enzymes that cleave oligopeptides include proteases and peptidases. Examples of enzymes that cleave oligosaccharides include sugar hydrolases and glycosidases 4. Targeting Ligand The term "targeting ligand" means a molecule which serves to deliver the compound of the invention to a specific site for the desired activity. Targeting ligands include, for example, molecules that specifically bind molecules on a specific cell surface. Example targeting ligands include antibodies, antibody fragments, small organic molecules, peptides, peptoids, proteins, polypeptides, oligosaccharides, transferrin, HS-glycoprotein, coagulation factors, serum proteins, beta-glycoprotein, G-CSF, GM-CSF, M-CSF, EPO, and the like. In some embodiments, the targeting ligand is RGDfK, EPPT1 peptide, or folate, which is attached to the polymer, optionally via a linker.

Generally with passively targeted HPMA conjugates success in clinical trials has been marginal primarily because of the limited accumulation of the drug in solid tumors by passive diffusion alone and heterogeneity of clinical presenting cancers. Active targeting strategies may allow targeting to multiple cell types taking into account the variations in tumor physiology, maximize distribution in the microenvironment of solid tumors while concurrently minimizing their non-specific uptake in other organs. Active targeting strategies will also significantly improve the therapeutic efficacy by (1) increasing tumor specificity; (2) improving pharmacokinetics; and (3) reducing toxicity. Several such strategies have emerged over the recent years that can be exploited to significantly improve tumor localization of anticancer drugs. Active targeting of polymeric drug delivery systems by attaching molecular markers (e.g., peptides and antibodies) has shown to significantly improve tumor localization.

Mucin-1 is a transmembrane molecule, expressed by most glandular epithelial cells. Several important features make mucin-1 an attractive receptor for targeted delivery to tumors.

First, mucin-1 is overexpressed on almost all human epithelial cell adenocarcinomas, including 90% of human breast, ovarian, pancreatic, colorectal, lung, prostate, colon, and gastric carcinomas. Moreover, mucin-1 expression has been demonstrated in nonepithelial cancer cell lines (astrocytoma, melanoma, and neuroblastoma), as well as in hematological malignancies such as multiple myeloma and some B-cell non-Hodgkin lymphomas, in total constituting 50% of all cancers in humans.

Second, in adenocarcinomatous tissue, as the result of the lost gland architecture, mucin-1 is ubiquitously expressed all over the cell surface. Because of its rod-like structure, the molecule extends 100-200 nm above the surface, which is 5-10-fold the length of most membrane molecules. This feature makes mucin-1 an accessible target for therapeutic probes.

Third, whereas in normal tissues mucin-1 is heavily glycosylated (50-90% of its molecular mass is due to carbohydrates), mucin-1 is typically underglycosylated in neoplastic tissues. Reduced glycosylation permits the immune system to access the peptide core of the tumor-associated underglycosylated mucin-1 antigen and reveals epitopes, which in the normal cell are masked. This feature makes it possible to design probes that discriminate between normal cells and adenocarcinoma cells.

Fourth, the extracellular domain of mucin-1, defined by the presence of the APDTRP (SEQ ID NO: 10) sequence, extends above the cell surface, thus interfering with the interaction between adhesion molecules on the tumor cell surface and their ligands on lymphocytes, aiding in the inaccessibility of tumor epitopes to immune recognition. Therefore, there is no tendency for tumor antigen down-regulation in response to immunotherapy, and mucin-1 expression remains homogeneously up-regulated during the life of the tumor and tumor metastases. These features are important in designing targeted drug delivery for different stages of tumor progression.

An abundant number of investigations have focused on the potential to use mucin-1 as a target for immunotherapy. Multiple monoclonal antibodies have been produced to recognize the immunogenic APDTRP (SEQ ID NO: 10) sequence of the tandem repeat. However, when antibodies were used as targeting molecules, the immunogenicity and long plasma half-life of these proteins were detrimental. Consequently, the use of small peptides instead may eliminate these shortcomings because peptide ligands are nonimmunogenic and have high affinity and selectivity for receptors. Synthetic peptide, designated EPPT1 (YCAREPPTRTFAYWG; SEQ ID NO: 11), has been developed as specific ligands and has shown significant affinity (Kd=20 µM). EPPT1 peptide, labeled with (99mTc), has been used to image breast carcinomas in vivo. All of the features of the mucin-1 protein listed above make this molecule an ideal candidate for a potential tumor targeting ligand.

A number of tumor cell and associated vasculature specific receptors have also been identified that differentiate tumor cells from normal cells. The αVβ3 integrin is one of the most studied and is selectively overexpressed in tumor associated neovasculature as well as in certain metastatic cancers (Felding-Habermann et al., Clin. Exp. Metastasis, 19: 427-436 (2002)). High affinity αVβ3 selective ligands containing the tripeptide sequence, Arg-Gly-Asp (RGD), have been identified by phage display studies. The conformationally restrained RGD sequence, i.e. cyclic RGD, contains disulfide bridges and binds to αVβ3 20-40 fold more avidly than linear RGD peptides (Koivunen, E., Wang, B. & Ruoslahti, E., Biotechnology (N.Y.), 13: 265-270 (1995)). RGD peptide has been conjugated with doxorubicin (Arap, W., Pasqualini, R. & Ruoslahti, E., Science, 279: 377-380 (1998)) for targeted chemotherapy as well as for targeted radiotherapy (Capello, A. et al., J. Nucl. Med., 45: 1716-1720 (2004)). They have been conjugated to humanized antibodies, liposomes, poly (ethylene glycol) and HPMA copolymers to improve biodistribution and increase tumor accumulation and antitumor efficacy. These studies make RGD and cyclic RGD an ideal targeting ligand for studying anti-tumor drug targeting.

Folic acid and its reduced counterparts are required by eukaryotic cells for one carbon transferreactions used in the biosynthesis of nucleotide bases. Cellular uptake of folates is facilitated by either a low affinity reduced folate carrier (Km~1 µM), which is present in virtually all cells of the body, or a high affinity glycosylphosphatidylinositol- linked folate receptor (FR) (KD=~100 pM), which exhibits highly limited distribution. FRs exhibit limited expression on healthy cells, but are often present in large numbers on cancer cells. For example, FRs are overexpressed on epithelial cancers of the ovary, mammary gland, colon, lung, prostate, nose, throat, and brain. FRs are also overexpressed on hematopoietic malignancies of myeloid origin, including chronic and acute myelogenous leukemias. A strong correlation has been observed between FR expression and the grade and histological stage of a tumor. A variety of folate linked molecules and complexes have been designed to enable selective delivery of drugs to FRs on cancer cells and activated macrophages. Other features that render folic acid an attractive ligand for use in drug targeting include its low molecular weight (MW 441), water solubility, stability to diverse solvents, pHs, and heat, facile conjugation chemistry, lack of immunogenicity, and high affinity for its receptor.

In some embodiments that include a targeting ligand, the targeting ligand may be RGDfK, EPPT1, or folate. In some embodiments, the targeting ligand is attached to the carrier polymer by a linker, which is an amino acid or peptide. In some embodiments, the linker is a peptide comprising Gly-Gly.

5. Efficiency and Specificity of Uptake by the Cells

The polymer based therapeutic compounds described herein can be characterized in that they allow for the uptake of anticancer agents by cells using typically different mechanisms than used by the anticancer agent alone. There are many ways to determine whether the efficiency and/or specificity of the uptake are increased by the polymer carrier. Typical increases of efficiency and/or specificity can be greater than or equal to at least 2 fold, 5 fold, 10 fold, 25 fold, 50 fold, 100 fold, 500 fold, 1000 fold, 5,000 fold or 10,000 fold.

6. Combination of Two Anticancer Agents

In some embodiments, the polymer based therapeutic composition has either a single copolymer having two (or more) anticancer agents attached thereto or a mixture of two or more copolymers, one containing a first anticancer agent and the other containing a second different anticancer agent. In some embodiments, the two anticancer agents differ in mechanism of action, or anticancer effect, etc. The anticancer agents can be bound to the polymeric carrier(s) via bonds stable in the blood stream, but susceptible to cleavage by lysosomal enzymes. When so formulated, both anticancer agents enter the same cells almost concurrently because the body distribution of both anticancer agents will generally be the same. This is fundamentally different compared to the combination therapy of two low molecular weight drugs not attached to polymer chains because the body distribution of each drug can be different if the drugs are not each attached to a polymer carrier. Moreover, after reaching the lysosomal compartment of the cell, the anticancer agents bound via an enzymatically degradable bond are released from the carrier by the action of lysosomal enzymes and diffuse through the lysosomal membrane into the cytoplasm. One of the main advantages of this approach is the optimization of the action of both anticancer agents by using anticancer agents that have different mechanism of action in cancer treatment. This will cause the death of cancer cells which were not destroyed by one anticancer drug.

The combination effect of anticancer agents may be obtained by administration of two separate copolymers, one containing an anticancer agent and the other containing another anticancer agent, when administered at the same time, when compared to the administration of each polymer administered separately in treating neoplastic diseases. Also, a single copolymer containing two different anticancer agents can be utilized instead of a mixture of copolymers. The specificity of these copolymers may be improved by the attachment of a targeting ligand to each polymer molecule.

Polymeric macromolecules typically are believed to enter targeted cells by pinocytosis; binding low molecular weight anticancer agents to copolymers alters their manner of uptake from diffusion to pinocytosis which may reduce the side effects normally elicited by the free anticancer agents. For this reason it is possible to use much lower doses of both anticancer agents when attached to the "combination" copolymer. In addition, it is possible to use even lower doses if the two anticancer agents have a synergistic anticancer effect. Attaching both anticancer agents to the same copolymer ensures that both anticancer agents will enter the same cell at the same time. A targeting ligand specific for a tumor marker on the cancer cell also bound to the "combination" copolymer side chains will facilitate or enhance the direction of the copolymer containing both anticancer agents specifically to the targeted cancer cells.

In U.S. Pat. No. 5,258,453, the antitumor efficacy of the combination copolymers (such as HPMA copolymers), containing an anticancer drug (such as adriamycin) and containing a photosensitizer (such as meso-chlorin e6 monoethylene diamine disodium salt ($ce_6$)) in vivo was found to be superior to the use of copolymers containing the photosensitizer and polymers containing the anti-cancer drug administered alone.

The present invention can also minimize the amount of cancer cells which are resistant to chemotherapy, thus decreasing substantially the possibility of tumor recurrence. This approach can be more successful in the treatment of multidrug resistant cells (MDR) than presently available therapies. The concentration of anticancer agents in the cell, when this method is used, is increased, even if the transport of the anticancer agents into the cell interior or MDR cells is impaired. If a suitable targeting ligand is attached (e.g. structures complementary to cell surface antigens or receptors), then a combined intracellular and extracellular action will increase the efficacy (the intracellular action will proceed by the above described mechanism, the extracellular action will be on the plasma membrane).

C. Method of Making Compounds

The present invention includes the synthesis of N-2-carboxypropyl methacrylamide (2-CPMA), N-(3-carboxypropyl)methacrylamide (3-CPMA), and N-(2-aminopropyl)methacrylamide (2-APMA).

In most instances, the main comonomer unit determines the properties of the polymeric carriers. Several comonomer units may be used resulting in water soluble copolymers. The copolymer can be made by copolymerization of the desired mole ratio of underivatized comonomer units with the desired ratio of comonomer units which have been derivatized to contain appropriate attachment groupings or spacers or linkers, which, in turn, possess reactive groups to which bioactive agents, such as anticancer agents, or targeting moieties may be subsequently attached. In alternative embodiments, the use of comonomers with different functional groups allows for selectively derivatizing one comonomer. Thus, the polymer can also be derivatized after polymerization. Typical comonomer units may be made of N-(2-hydroxypropyl)methacrylamide (HPMA), N-(2-carboxypropyl)methacrylamide (2-CPMA), N-(3-carboxypropyl)methacrylamide (3-CPMA), N-(2-aminopropyl)methacrylamide (2-APMA) or N-(3-aminopropyl)methacrylamide (3-APMA). Other suitable carriers include polyamino acids, polysaccharides, copolymers containing polyethyleneoxide sequences, polyvinyl pyrrolidone-maleic anhydride copolymers, and the like.

The comonomers utilized in this invention include N-(2-hydroxypropyl)methacrylamide (HPMA), N-(2-carboxypropyl)methacrylamide (2-CPMA), N-(3-carboxypropyl)methacrylamide (3-CPMA), (N-(2-aminopropyl)methacrylamide (2-APMA)) or N-(3-aminopropyl)methacrylamide (3-APMA) (available from Polysciences, Inc (PA)).

The basic comonomer, N-(2-aminopropyl)methacrylamide (2-APMA), can be made, for example by the following process.

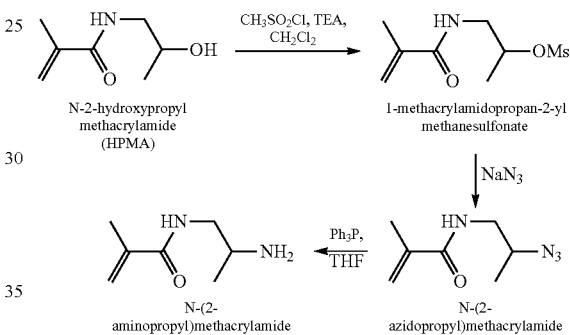

Embodiments include the acidic drug carrier, such as 2-CPMA or 3-CPMA polymers and copolymers, or other drug carriers such as neutral HPMA polymers and copolymers, and basic drug carrier such as 3-APMA or 2-APMA polymers and copolymers, where the polymer or copolymer includes at least one of 2-CPMA, 3-CPMA, 2-APMA or 3-APMA monomers, as useful polymeric systems for the delivery of one or two anticancer agents.

Using the monomer units, N-(2-hydroxypropyl)methacrylamide (HPMA), N-(2-carboxypropyl)methacrylamide (2-CPMA), N-(3-carboxypropyl)methacrylamide (3-CPMA), N-(3-aminopropyl)methacrylamide (3-APMA), or N-(2-aminopropyl)methacrylamide (2-APMA), polymers and copolymers can be prepared and used as carriers for the delivery of anticancer agents to the cancer cell. Copolymers containing two or more of HPMA, 2-CPMA, 3-CPMA, 2-APMA and 3-APMA can also be prepared in similar manner.

The compositions of the invention can be prepared using techniques known in the art. As described, there are up to four components used to produce the compositions: the anticancer agent, the polymer carrier, the targeting moiety and a linker molecule. Any of the components can be reacted with one another in any suitable order or combination to produce the compounds of the invention. It is sometimes preferred to couple (i.e., react) two of the components together to produce a new reaction product or intermediate, and then chemically connect the intermediate with the next component. Polymerization can be performed either before or after derivatization of a monomer with a linker, anticancer agent, and/or targeting ligand.

For example, the anticancer agent can be reacted with a monomer, (for example, 2-CPMA, 3-CPMA, 2-APMA, 3-APMA or HPMA) to produce a derivatized monomer, in this case an anticancer/monomer molecule. The anticancer/monomer molecule can then be polymerized with the same or other monomers to produce a composition according to the invention. Alternatively, the anticancer agent can be reacted with a linker molecule to produce an anticancer/linker molecule, which can then be reacted with a monomer to produce a derivatized monomer, in this case a an anticancer/linker/monomer molecule. The anticancer/linker/monomer molecule can then be polymerized with the same or other monomers to produce a composition according to the invention. As yet another alternative, one or more monomers can be polymerized and the resultant polymer reacted with an anticancer agent or linker/anticancer agent molecule to form a composition according to the invention. Targeting ligands (optionally through a linker) can be incorporated into the composition in a similar manner by preparing monomer molecules followed by polymerization or by reaction with a preformed polymer.

As is apparent, there are a number of combinations and ordering of steps that can be used to produce carrier polymer compositions according to the invention. In embodiments where the composition includes more than one carrier polymers, each polymer can be separately produced and then combined to generate the composition.

For example, in one embodiment, the compound can be produced by (1) reacting the linker with a monomer to produce a monomer/linker molecule, (2) reacting the monomer/linker molecule with an anticancer agent and (3) polymerizing the monomers (with any comonomers), followed by adding a targeting ligand.

In a specific example, the polymer-based therapeutic compound can be produced by reacting methacryloyl chloride (MACl) with Gly-Phe (GF) and coupling the product with Leu-Gly (LG) to produce an MA-GFLG-OH molecule (see Scheme 3 below). The MA-GFLG-OH molecule is then reacted with gemcitabine or docetaxel to produce the MA-GFLG-anticancer molecule(s). The MA-GFLG-anticancer molecule(s) is then reacted (polymerized) with at least one of 2-CPMA, 3-CPMA, 2-APMA, or 3-APMA comonomer, and optionally other comonomers to produce a polymer-based therapeutic compound in the form of a copolymer-drug(s) conjugate. The copolymer-drug(s) conjugate may then be reacted with a targeting ligand, such as, for example, RGDfK, EPPT1 peptide or folate a polymer-based therapeutic compound containing a targeting ligand. 'GFLG' is disclosed as SEQ ID NO: 1

In another embodiment, MA-GFLG-OH is reacted with Docetexal (DCT) to give MA-GFLG-DCT and MA-GFLG-ONp with Gemcitabine (GEM) to give MA-GFLG-GEM. MA-GFLG-ONp is the p-nitrophenyl ester of MA-GFLG-OH. These two monomers are reacted (or polymerized) with 2-CPMA, 3-CPMA, 2-APMA, and/or 3-APMA comonomer to produce a copolymer. Additional comonomers may be included in the reaction, such as, for example, HPMA and/or methacryloyl-glycylglycine-O-p-nitrophenylester (MA-GG-ONp) to produce other copolymers. A copolymer produced from a reaction including MA-GG-ONp can be further reacted with a targeting ligand to produce a polymer-based therapeutic compound. HPMA or 2-CPMA or 3-CPMA or 2-APMA or 3-APMA -GFLG-drug containing a targeting ligand, including, for example, RGDfK, EPPT1 peptide or folate. 'GFLG' is disclosed as SEQ ID NO: 1

As described above, the anticancer agent, polymer carrier, and linker can be attached to one another directly or indirectly. In addition, the attachment of each component to one another can vary depending upon the types of components selected and the order in which the components are permitted to react with one another.

D. Method of Using Compounds

The disclosed polymer-based therapeutic compounds can be used for passive or targeted delivery of anticancer agents to cells. These compounds can be used to treat a variety of disorders that require the delivery of anticancer or similar agents. It is understood that any of the compounds disclosed can be used in this way. Those of skill in the art understand the compounds will be administered in pharmaceutically acceptable forms (i.e. in a pharmaceutical composition) and in doses wherein delivery occurs. Typically the compounds would be administered to patients in need of delivery of the anticancer agent or a similar compound. It is understood that the goal is delivery of the compound to the cells of the patient in need of the anticancer agent or similar agent.

The polymer based therapeutic compounds, bearing conjugated anticancer agents, can be given to a subject. Any subject in need of receiving an anticancer agent can be given the disclosed conjugated anticancer agents. The subject can, for example, be a mammal, such as a mouse, rat, rabbit hamster, dog, cat, pig, cow, sheep, goat, horse, or primate, such as monkey, gorilla, orangutan, chimpanzee, or human.

The polymer based therapeutic compounds, bearing conjugated anticancer agents, can be used for inhibiting cancer cell proliferation. Inhibiting cancer cell proliferation means reducing or preventing cancer cell growth. Inhibitors can be determined by using a cancer cell assay. For example, either a cancer cell line can be cultured on 96-well plates in the presence or absence of the conjugated anticancer agent or anticancer agent alone or anticancer agent prepared differently then the disclosed compositions (for example, just anticancer agent and carrier) for any set period of time. The cells can then be assayed. In certain embodiments the conjugated anticancer compounds are those that will inhibit 10% or 15% or 20% or 25% or 30% or 35% or 40% or 45% or 50% or 55% or 60% or 65% or 70% or 75% or 80% or 85% or 90% or 95% of growth relative to any of the controls as determined by the assay.

Disclosed are compositions which inhibit metastatic tumor formation in this type of assay disclosed herein, as well as compositions that reduce metastatic tumor formation by at least 10% or 15% or 20% or 25% or 30% or 35% or 40% or 45% or 50% or 55% or 60% or 65% or 70% or 75% or 80% or 85% or 90% or 95% of a control compound.

The disclosed compositions can be used to treat any disease where uncontrolled cellular proliferation occurs such as cancers or neoplastic disorders. A non-limiting list of different types of cancers is as follows: carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumours, myelomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and nonsmall cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

Compositions disclosed herein may also be used for the treatment of precancer conditions such as cervical and anal dysplasias, other dysplasias, severe dysplasias, hyperplasias, atypical hyperplasias, and neoplasias.

E. Dosages

The dosage ranges for the administration of the compositions are those large enough to produce the desired effect in which delivery occurs. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary from about 1 mg/kg to 30 mg/kg in one or more dose administrations daily, for one or several days.

F. Pharmaceutically Acceptable Carriers

Any of the compositions can be used therapeutically in combination with a pharmaceutically acceptable carrier to form a pharmaceutical composition.

Pharmaceutical carriers are known to those skilled in the art. These most typically would be standard carriers for administration of compositions to humans, including solutions such as sterile water, saline, and buffered solutions at physiological pH. Other compounds will be administered according to standard procedures used by those skilled in the art.

Compositions intended for pharmaceutical delivery may be formulated in a pharmaceutical composition. Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for parenteral administration include sterile aqueous or non-aqueous solutions, suspensions, and emulsions that may also contain buffers, diluents and other suitable additives. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions as described herein can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Pharmaceutical Compositions

The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

Injectable preparations, including, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

While the compositions of the invention can be administered as the sole active pharmaceutical agent, they can also be used in combination with one or more therapeutic agents, such as immunomodulators, antiviral agents or antiinfective agents.

The foregoing is merely illustrative of the invention and is not intended to limit the invention to the disclosed compositions. Variations and changes that are obvious to one skilled in the art are intended to be within the scope and nature of the invention which are defined in the appended claims. From the foregoing description, one skilled in the art can easily ascertain the essential characteristics of this invention, and without departing from the spirit and scope thereof, can make various changes and modifications of the invention to adapt it to various usages and conditions.

EXAMPLES

The invention may be further clarified by references to the following examples, which serve to exemplify some of the preferred embodiments, and not to limit the invention in any way.

Example 1

Synthesis of Polymer-Gemcitabine or Docetaxel or Gemcitabine/Docetaxel Conjugates.

1) Synthesis of N-(2-carboxypropyl)methacrylamide (2-CPMA) Comonomers

Synthesis of the reactive monomer 2-CPMA was described as shown in Scheme 1.

Scheme 1

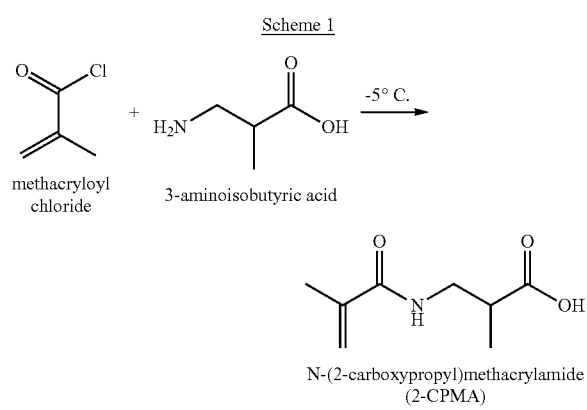

N-(2-carboxypropyl)methacrylamide
(2-CPMA)

3-Aminoisobutyric acid (5.5 g, 53.3 mmol) was dissolved in 26.8 ml of 2N NaOH (53.6 mmol) and cooled to −5° C. Freshly distilled methacryloyl chloride (MAC1) (7.9 g, 75.9 mmol) in 22 ml of dichloromethane was added dropwise. A small amount of inhibitor, tertiary octyl pyrocatechine was added to prevent polymerization of the monomer. Simultaneously but with a slight delay, 38.5 ml (76.9 mmol) of 2N NaOH was added dropwise to the reaction mixture. After addition of MACl and NaOH the reaction mixture was warmed up to room temperature and allowed to react for two hours. The pH was maintained at around 8-9. The dichloromethane layer was separated from the water layer, washed with water (20 ml×2) and discarded. The combined aqueous layer was mixed with 100 ml of ethyl acetate. Under vigorous stirring and cooling, dilute HCl was added slowly until the pH reached at 2. The organic layer was separated and the aqueous layer was extracted three times with ethyl acetate. The combined organic layer was dried over anhydrous sodium sulfate overnight. The dried solution was filtered and washed with ethyl acetate. The ethyl acetate was removed by rotary evaporation to obtain the product as a white powder. Recrystallization was done from ethyl acetate (8.5 g, 93.2% yield). $^1$H NMR (400 MHz, CDCl$_3$): δ 1.25(s, 3H), 1.96(s, 3H)), 2.79-2.80(m, 1H), 3.35-3.41(m, 1H), 3.59-3.65(m, H), 5.34 (s, 1H), 5.71(s, 1H), 6.44(s, 1H, NH).

N-(3-carboxypropyl)methacrylamide (3-CPMA) can be made as above, synthesis of 2-CPMA, using methacryloyl chloride and 4-aminobutyric acid.

2) Synthesis of N-(2-hydroxypropyl)methacrylamide (HPMA) Comonomers

Synthesis of the reactive monomer HPMA was as previously described (Kopecek and Bazilova, 1973) as shown in Scheme 2.

Scheme 2

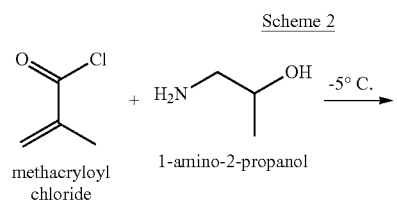

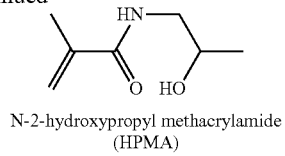

N-2-hydroxypropyl methacrylamide
(HPMA)

To a solution of 1-amino-2-propanol (128.4 g, 1.71 mol) in 500 ml of acetonitrile, freshly distilled methacryloyl chloride (MACl) (90.8, 0.86 mol) in 40 ml of acetonitrile was added drop wise under vigorous stifling at −5° C. A small amount of inhibitor, tertiary octyl pyrocatechine was added to the solution. The reaction mixture was stirred for an additional 30 min at room temperature. 1-Amino-2-propanol hydrochloride formed as a byproduct was precipitated and filtered off. The residue was washed with pre-cooled acetonitrile. The filtrate was cooled to −70° C. and the HPMA precipitated. After equilibrating to room temperature the product was filtered off and washed with pre-cooled acetonitrile. Recrystallization was from acetone and the pure product was isolated (75.9 g, 61.6% yield). MS(ESI) m/z 144 (M+1). $^1$H NMR (400 MHz, CDCl$_3$): δ 1.20 and 1.22(d, J=6.4 Hz, 3H)), 1.97(s, 3H), 3.18-3.21(m, 1H), 3.48-3.51(m, 1H), 3.95-3.96(m, 1H), 5.36 (s, 1H), 5.74(s, 1H).

3) Synthesis of MA-GF-OH

Methacryloylglycylphenylalanine (MA-GF-OH) was made from the reaction of methacryloyl chloride (MACl) and glycylphenylalanine (GF) as outlined in Scheme 3.

Glycylphenylalanine (Gly-Phe), 5.0 g, 22.5 mmol) was dissolved in 11.3 ml of 2N NaOH (22.5 mmol) and cooled to 0-5° C. Freshly distilled MACl (2.8 g, 26.8 mmol) in 10 ml of dichloromethane was added dropwise. A small amount of inhibitor, tertiary octyl pyrocatechine was added to prevent polymerization of the monomer. Simultaneously but with a slight delay, 13.5 ml (26.9 mmol) of 2N NaOH was added dropwise to the reaction mixture. After addition of MACl and NaOH the reaction mixture was warmed up to room temperature and allowed to react for two hours. The pH was maintained at around 8-9. The dichloromethane layer was separated from the water layer, washed with water (7 ml×2) and discarded. The combined aqueous layer was mixed with 50 ml of ethyl acetate. Under vigorous stirring and cooling, dilute HCl was added slowly until the pH reached at 2-3. The organic layer was separated and the aqueous layer was extracted three times with ethyl acetate. The combined organic layer was dried over anhydrous sodium sulfate overnight. The dried solution was filtered and washed with ethyl acetate. The ethyl acetate was removed by rotary evaporation to obtain the product as a white powder. Recrystallization was done from ethyl acetate (6.3 g, 96.5% yield, melting point: 141.8-143.4° C.). $^1$H NMR (400 MHz, CDCl$_3$): δ 1.96(s, 3H)), 3.06-3.20(2m, 2H), 3.85-4.11(2m, 2H), 4.83-4.85(m, 1H), 5.41 (s, 1H), 5.79(s, 1H), 7.20-7.30(m, 5H).

4) Synthesis of LG-OMe HCl

Leucylglycine-OMe (LG-OMe) was made from the reaction of leucylglycine (LG) and methanol/thionyl chloride as outlined in Scheme 3.

Leucylglycine (Leu-Gly, 5.0 g, 26.6 mmol) was dissolved in 40 ml of methanol and cooled to −15 ° C. An excess of thionyl chloride (SOCl$_2$) (4 ml, 54.8 mmol) was added dropwise for 15 min under stifling. After equilibrating to room temperature the mixture was refluxed for 3.5 hours. The solvent was evaporated to dryness and the residue was dissolved in methanol and evaporated again to remove traces of HCl and SOCl$_2$. The residue was mixed with ethyl ether and the removal of ethyl ether layer and evaporation gave a white amorphous solid. The crude product (LG-OMe.HCl, 6.53 g) was used in subsequent steps without purification. $^1$H NMR (400 MHz, DMSO-d$_6$): δ 0.89-0.93(m, 6H), 1.56-1.61(m, 2H)), 1.71-1.78(m, 1H), 3.65(s, 3H), 3.77-3.85(m, 2H), 3.88-4.00(m, 1H), 5.41 (s, 1H), 5.79(s, 1H), 7.25-7.28(m, 5H).

5) Synthesis of MA-GFLG-OMe (SEQ ID NO: 1)

Methacryloylglycylphenylalanylleucylglycine OMe (MA-GFLG-OMe) was made from the reaction of methacryloylglycylphenylalanine (MA-GF-OH) and leucylglycine-OMe (LG-OMe) as outlined in Scheme 3. 'GFLG' is disclosed as SEQ ID NO: 1.

5.1 g of crude Leu-Gly-OMe HCl (21.5 mmol) in 3.88 g of N,N'-diisopropylethylamine (DIPEA, 30 mmol) and 50 ml of ethyl acetate was mixed with 5.0 g of MA-Gly-Phe (17.2 mmol) in 200 ml of ethyl acetate under stifling at room temperature. To the mixture, 18.3 g of (benzotriazol-1-yloxy)tris(dimethylamino)phosphonium hexafluorophosphate (BOP, 41.3 mmol) was added and the reaction mixture was stirred for 3 days at room temperature. The reaction mixture was washed with 5% NaHCO$_3$ solution (200 ml×3), water, 1 M NaHSO$_4$ (200 ml×3) and saline. The organic layer was dried over anhydrous sodium sulfate. After filtering off the drying agent and the filtrate was concentrated under vacuum to obtain the product (MA-GFLG-OMe). The purification by SiO$_2$ column chromatography gave 6.35 g of MA-GFLG-OMe (77.8% yield, melting point: 140.9-143.0° C.). 'GFLG' is disclosed as SEQ ID NO: 1.

6) Synthesis of MA-GFLG-OH (SEQ ID NO: 1)

Methacryloylglycylphenylalanylleucylglycine (MA-GFLG-OH) (SEQ ID NO: 1)was made from the hydrolysis of methacryloylglycylphenylalanylleucylglycine OMe (MA-GFLG-OMe) (SEQ ID NO: 1) as outlined in Scheme 3.

To a cooled solution of 5.1 g of MA-GFLG-OMe (SEQ ID NO: 1) (10.7 mmol) in 109 ml of methanol, excess of 1 N NaOH (12.9 ml, 12.9 mmol) was added dropwise under stirring at 0° C. After addition of a small amount of inhibitor (t-octyl pyrocatechine) the reaction mixture was stirred for two hours at 0° C. and then for four hours at room temperature. The reaction mixture was concentrated under vacuum to remove methanol, mixed with 150 ml of distilled water. The water layer was washed with ethyl acetate (100 ml×2) and acidified with 1.0 M citric acid to pH 2.0-2.5. The free acid was extracted with 3×150 ml of ethyl acetate, washed with saturated brine and dried over anhydrous sodium sulfate overnight. After evaporation of the solvent under vacuum the tetrapeptide product (MA-GFLG-OH) (SEQ ID NO: 1) was recrystallized from ethyl alcohol/n-hexane (1:1) mixture (3.06 g, melting point: 161.4-165.6° C.). MS(ESI) m/z 483 (M+Na).

Scheme 3. 'GFLG' is disclosed as SEQ ID NO: 1.

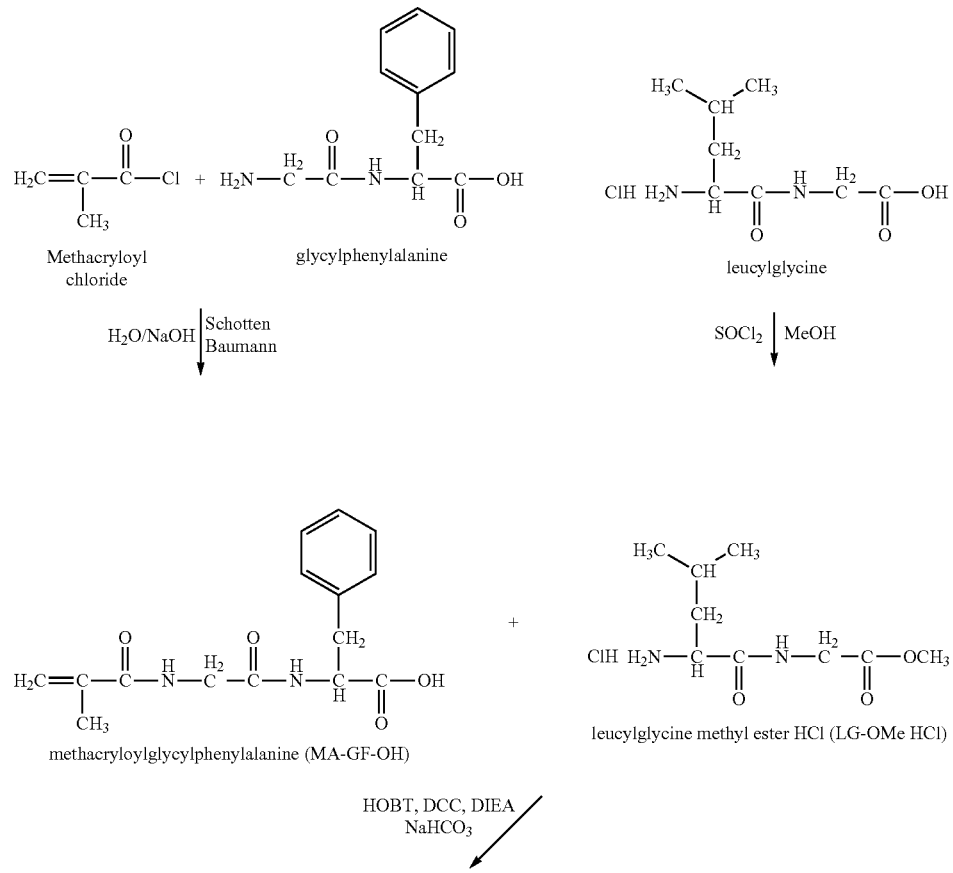

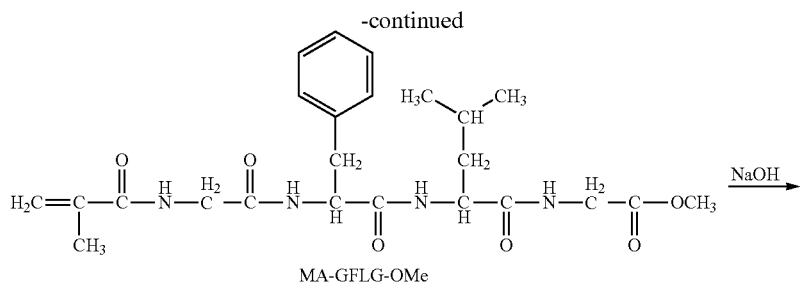

MA-GFLG-OMe

→ NaOH

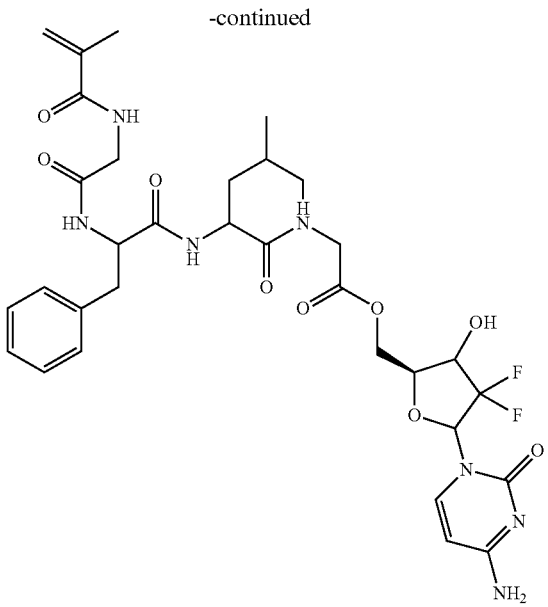

MA-GFLG-OH

7) Synthesis of methacryloylglycylphenylalanylleucylglycyl-Gemcitabine (MA-GFLG-Gemcitabine (SEQ ID NO: 1)) (Scheme 4).

730 mg of MA-GFLG-OH (SEQ ID NO: 1) (1.52 mmol), 414 mg of gemcitabine HCl (1.38 mmol), 732 mg of BOP (1.66 mmol) and a small amount of tertiary octyl pyrocatechine were dissolved in the mixture of 0.5 ml of DIPEA and 30 ml of acetonitrile under nitrogen at room temperature. The mixture was stirred for 1 day at room temperature and concentrated under vacuum to remove the solvent. The product was purified by column chromatography (silica gel, eluent: EtOAc/MeOH=4/1) and analyzed by mass spectrometry (M+1=706.3) and tlc. The yield was 962 mg (98.8%).

Scheme 4. 'GFLG' is disclosed as SEQ ID NO: 1.

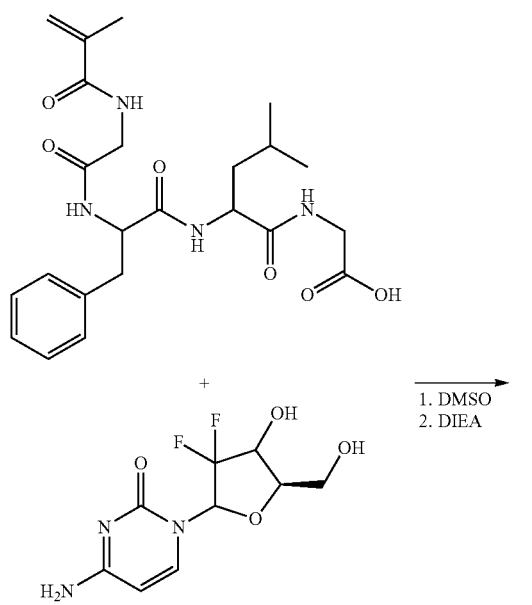

+

1. DMSO
2. DIEA

MA-GFLG-Gemcitabine

8) Synthesis of methacryloylglycylphenylalanylleucylglycyl-Docetaxel (MA-GFLG-Docetaxel (SEQ ID NO: 1)) (Scheme 5).

363 mg of MA-GFLG-OH (SEQ ID NO: 1) (0.76 mmol), 555 mg of docetaxel (0.69 mmol), 574 mg of BOP (1.30 mmol), 114 mg of 4-dimethylaminopyridine (DMAP, 0.94 mmol) and a small amount of tertiary octyl pyrocatechine were dissolved in the mixture of 10 ml of ethyl acetate and 12 ml of acetonitrile under nitrogen at 4° C. The reaction mixture was stirred for 1 h at 4° C. and then for 2 days at room temperature and concentrated under vacuum to remove the solvent. The product was purified by column chromatography (silica gel, eluent: EtOAc/MeOH=10/1) to give 803 mg of the product (91.5% yield). The product was verified by thin layer chromatography and mass spectroscopy m/z 1272.3 (M+Na).

Scheme 5. 'GFLG' is disclosed as SEQ ID NO: 1.

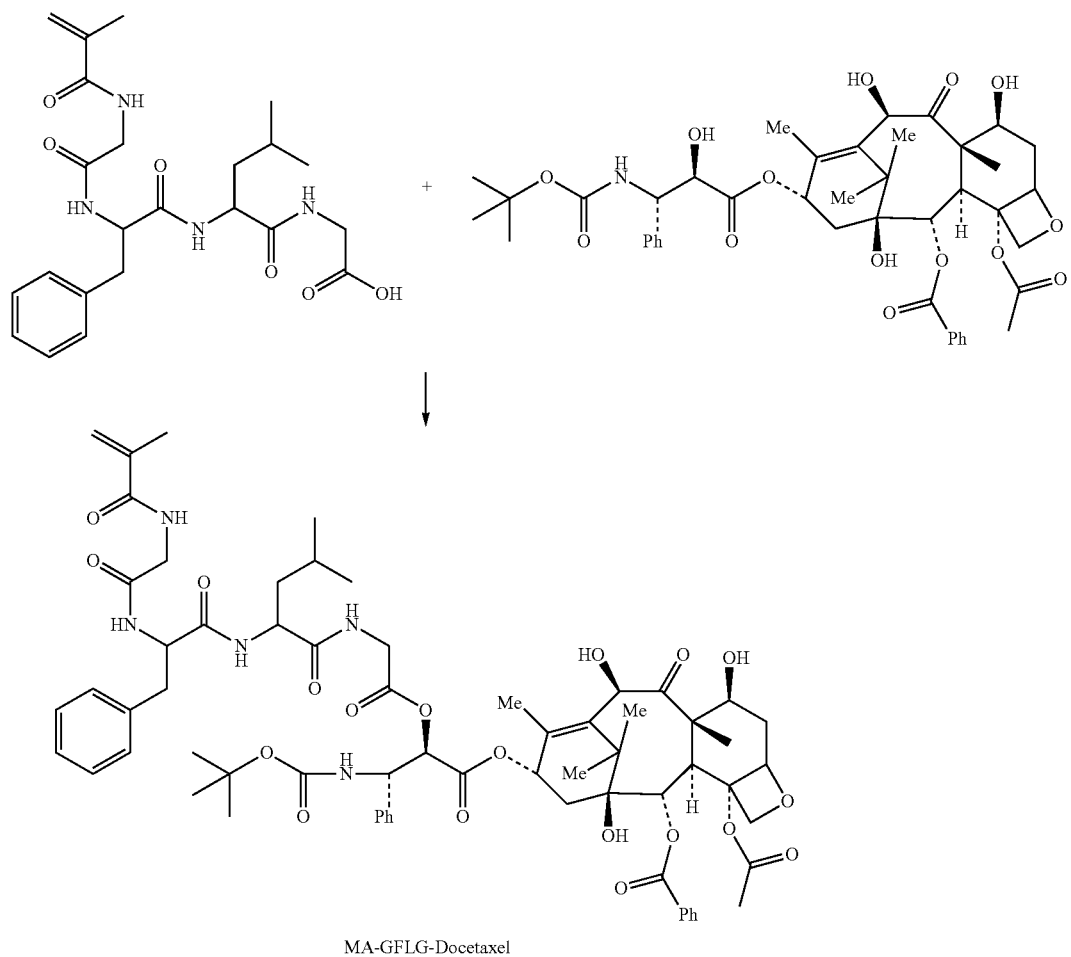

MA-GFLG-Docetaxel

9) Polymer-Gly-Phe-Leu-Gly-Gemcitabine (SEQ ID NO: 1) Preparation

HPMA, 2-APMA, 3-APMA 2-CPMA or 3-CPMA copolymer-gemcitabine conjugate are synthesized from the comonomers, by free radical precipitation copolymerization of the comonomers HPMA, 2-APMA, 3-APMA 2-CPMA or 3-CPMA (1.00 mmol) and MA-GFLG-gemcitabine (SEQ ID NO: 1) (78.4 mg, 0.112 mmol) in acetone (2 ml) at 50° C. for 24 h using N,N'-azobisisobutyronitrile (AIBN, 10.8 mg) as the initiator as shown in Scheme 6. Typically the ratio of comonomers: initiator: solvent is kept constant at 12.5:0.6:86.9 wt %. The mixture is sealed under nitrogen in an ampoule and left to polymerize with stifling at 50° C. for 24 h. The precipitated polymer is dissolved in methanol, repre-cipitated in 20×volume of ether and washed with ether. Small molecular weight unreacted monomers and other impurities are separated from the polymeric conjugates by redissolving in distilled water and dialyzing against distilled water to remove the salts and subsequently lyophilizing to obtain the pure product.

10) Polymer-Gly-Phe-Leu-Gly-Docetaxel (SEQ ID NO: 1) Preparation

HPMA, 3-APMA or 2-CPMA copolymer-docetaxel conjugate were synthesized from the comonomers, by free radical precipitation copolymerization of the comonomers HPMA (7.13 mmol), 3-APMA (5.93 mmol) or 2-CPMA (6.15 mmol) and MA-GFLG-docetaxel (SEQ ID NO: 1) (0.18 mmol for HPMA, 0.15 mmol for 3-APMA and 0.16 mol for 2-CPMA) in acetone (15 ml)/DMSO (1 ml) at 50° C. for 24 h using N,N'-azobisisobutyronitrile (AIBN, 60 mg) as the initiator as shown in Scheme 6. A tiny amount of 3-mercap-topropionic acid was used as a chain transfer agent. Typically the ratio of comonomers: initiator: solvent was kept constant at 8.8:0.4:90.8 wt %. The mixture was sealed under nitrogen in an ampoule and left to polymerize with stifling at 50° C. for 24 h. The precipitated polymer was dissolved in methanol, repreicipitated in 20×volume of ether and washed with ether. Small molecular weight unreacted monomers and other impurities were separated from the polymeric conjugates by redissolving in distilled water or 50 mM Tris HCl buffer (pH7.2) and dialyzed against distilled water or 50 mM Tris HCl buffer (pH7.2) and subsequently lyophilized to obtain the pure product.

Polymer-Gly-Phe-Leu-Gly-Docetaxel (SEQ ID NO: 1) using 2-APMA or 3-CPMA can be prepared in a similar manner.

11) Polymer-Gly-Phe-Leu-Gly-Docetaxel/Gemcitabine (SEQ ID NO: 1) Preparation HPMA, 2-APMA, 3-APMA, 2-CPMA, or 3-CPMA copolymer-docetaxel/gemcitabine conjugate are synthesized from the comonomers, by free radical precipitation copolymerization of the comonomers HPMA, 2-APMA, 3-APMA or 3-CPMA (1.00 mmol), MA-GFLG-gemcitabine (SEQ ID NO: 1) (0.089 mmol) and MA-GFLG-docetaxel (SEQ ID NO: 1) (0.022 mmol) in acetone (2 ml) at 50 °C. for 24 h using N,N'-azobisisobutyronitrile (AIBN, 10.8 mg) as the initiator as shown in Scheme 6. Typically the ratio of comonomers: initiator: solvent is kept constant at 12.5:0.6:86.9 wt %. The mixture is sealed under nitrogen in an ampoule and left to polymerize with stifling at 50° C. for 24 h. The precipitated polymer is dissolved in methanol, reprecipitated in 20×volume of ether and washed with ether. Small molecular weight unreacted monomers and other impurities are separated from the polymeric conjugates by redissolving in distilled water and dialyzing against distilled water to remove the salts and subsequently lyophilizing to obtain the pure product.

(SEQ ID NO: 1) and/or Gemcitabine and methacryloylglycylglycine-p-nitrophenyl ester (MA-GG-ONp) comonomers in acetone/5% DMSO. The feed compositions of the comonomers are about 89.34%, 0.66% and 10% respectively. N,N'-azobisisobutyronitrile (AIBN) is used as the initiator. Briefly comonomer HPMA, 2-APMA, 3-APMA 2-CPMA, or 3-CPMA (0.38 mmol), MA-GFLG-Docetaxel (SEQ ID NO: 1)and/or Gemcitabine (0.0028 mmol) and MA-GG-ONp (0.0424 mmol) and AIBN (3.43 mg) are dissolved in 1 ml of acetone (5% DMSO). The ratio of comonomers: initiator: solvent is kept constant at 12.5:0.6:86.9 wt %. The mixture is sealed under nitrogen in an ampoule and left to polymerize with stifling at 50° C. for 24 h. The precipitated polymer precursor is dissolved in methanol and reprecipitated in 20×volume of ether. Small molecular weight unreacted monomers and other impurities are separated from the polymeric conjugates by redissolving in distilled water and dialyzing against distilled water to remove the salts and subsequently lyophilizing to obtain the pure product. The ONp content of the polymer is determined spectrophotometrically at 272 nm.

In the second step the targeting peptide such as RGDfK is conjugated to polymer precursors by an aminolysis reaction. Briefly HPMA, 2-APMA, 3-APMA 2-CPMA, or 3-CPMA-

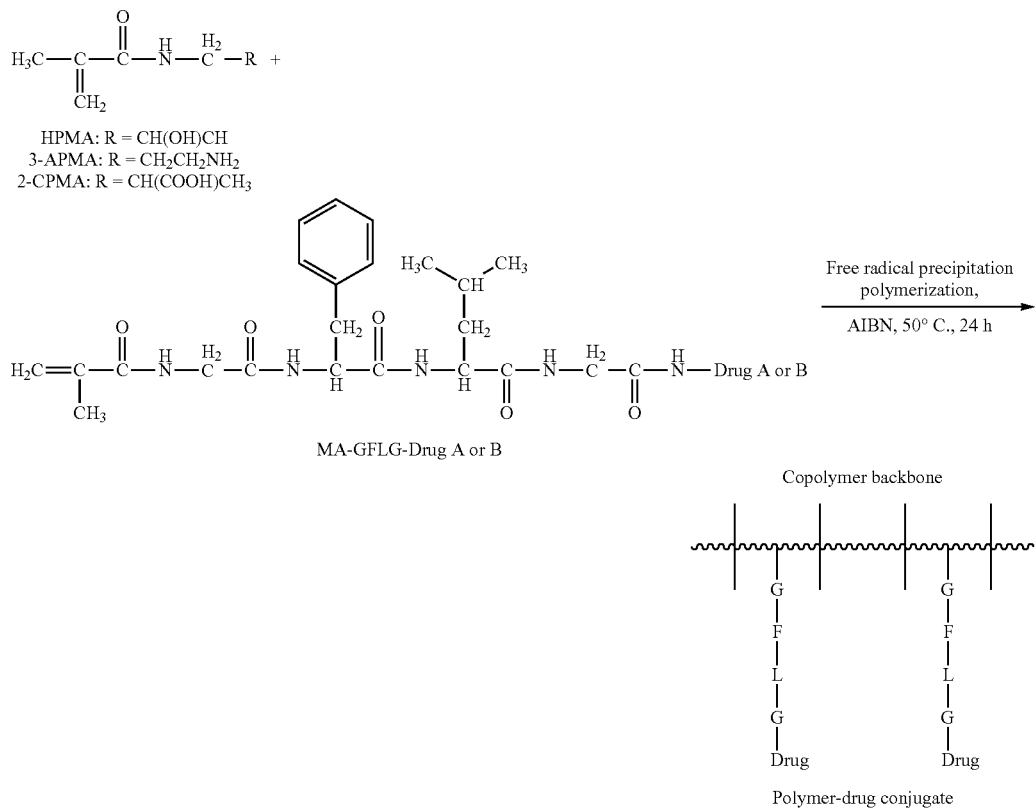

Scheme 6. 'GFLG' is disclosed as SEQ ID NO: 1.

12) Synthesis of HPMA copolymer-RGDfK-drug conjugate.

Polymeric conjugates are synthesized in a two step procedure as outlined in Scheme 7. In the first step the reactive HPMA, 2-APMA, 3-APMA 2-CPMA, or 3-CPMA copolymer-drug conjugates are synthesized by free radical precipitation copolymerization of comonomer HPMA, 2-APMA, 3-APMA 2-CPMA, or 3-CPMA, MA-GFLG-Docetaxel (GFLG-Docetaxel and/or Gemcitabine (SEQ ID NO: 1))-GG-ONp precursor (containing 0.02 mmol ONp groups) is dissolved in 1.6 ml dry DMF (dried over 3Å molecular sieves). RGDfK (0.03 mmol) is added at 1.3 molar excess to that of the MA-GG-ONp content in the polymeric precursor. The reaction is carried out under nitrogen for 24 h at room temperature. The reaction is terminated with 1-amino-2-propanol (0.02 mmol). The conjugate is dialyzed against deionized water and lyophilized.

Scheme 7. 'GFLG' is disclosed as SEQ ID NO: 1.

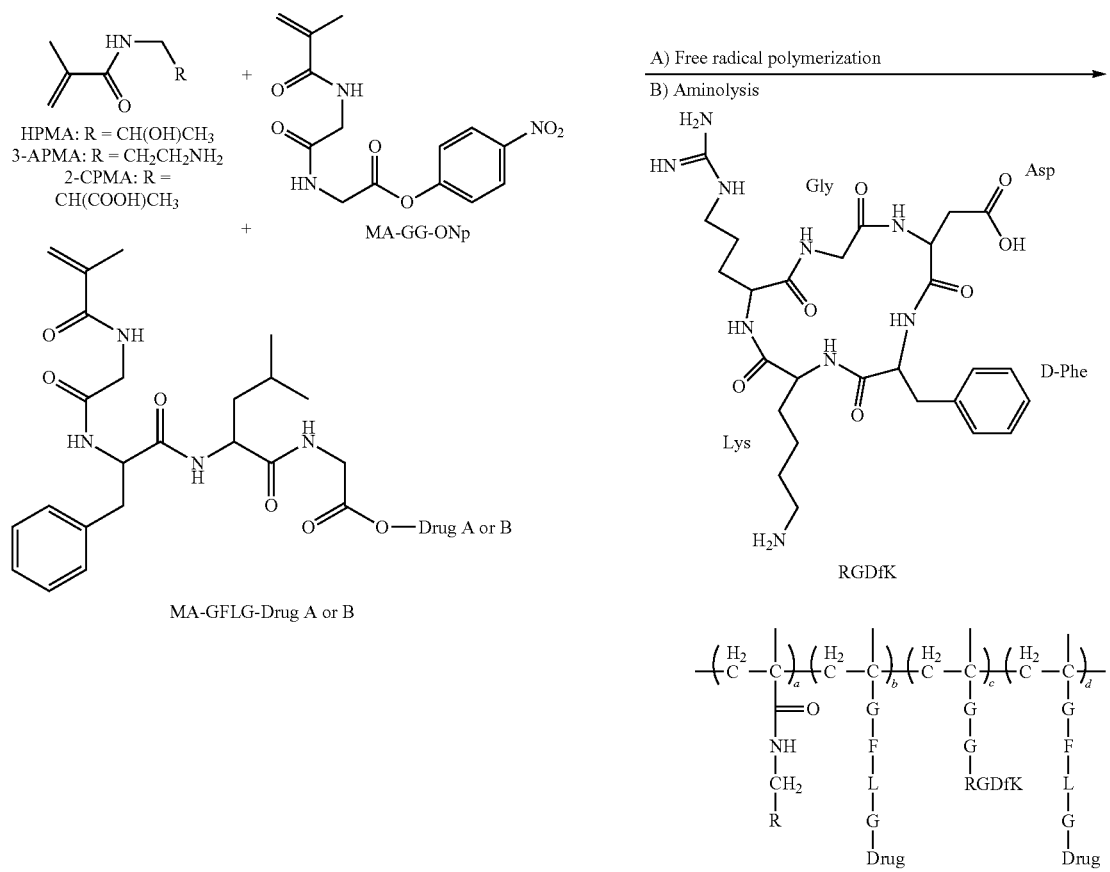

13) Physicochemical Characterization of Polymer-Drug Conjugates

The weight average molecular weight (Mw) and polydispersity of the synthesized polymer-drug conjugates were estimated by size-exclusion chromatography using a Superose 12 HR 10/30 column (Amersham Biosciences) on a Fast Protein Liquid Chromatography (FPLC) system (Amersham Biosciences). Samples at 1 mg/ml are eluted at a flow rate of 0.4 ml/min using PBS as the elution solvent. The number average molecular weight (Mn), weight average molecular weight (Mw) and polydispersity (n=Mw/Mn)) of the polymers were estimated from a calibration curve using poly-HPMA or poly2-CPMA or poly3-APMA fractions of known molecular weights. The drug content was obtained using Amino Acid Analysis (AIBio Tech., Richmond, Va.).

TABLE 1

Physicochemical characteristics of polymer-drug conjugates.

| | Feed Monomer Composition | | Polymer Characteristics | | |
| --- | --- | --- | --- | --- | --- |
| | (mole %) | | Drug Content | Mw | |
| Sample | Acrylate | MA-GFLG-Drug | (mmole/g polymer) | (g/mole) | Mw/Mn |
| pHPMA-GFLG-Docetaxel | 97.5 | 2.5 | 0.104 | 10 kD | 1.35 |
| p2-CPMA-GFLG-Docetaxel | 97.5 | 2.5 | 0.0659 | 13 kD | 1.24 |
| p3-APMA-GFLG-Docetaxel | 97.5 | 2.5 | 0.0446 | 10 kD | 1.22 |

'GFLG' is disclosed as SEQ ID NO: 1.

Example 2

Synthesis of Polymer-Drug A/Polymer-Drug B Conjugate (Scheme 8)

MA-GFLG-ONp is prepared from MA-GFLG-OH (as shown above). The MA-GFLG-Drug A or MA-GFLG-Drug B monomers can be prepared as outlined above. Poly(HPMA-co-MA-GFLG-ONp-MA-GFLG-Drug A) is prepared by free radical polymerization of MA-GFLG-ONp, MA-GFLG-Drug A, and HPMA using AIBN as an initiator. Poly(HPMA-co-MA-APMA-MA-GFLG-Drug B) is prepared by free radical polymerization of MA-GFLG-Drug B, HPMA and 3-APMA using AIBN as an initiator. Subsequently, poly(HPMA-co-MA-GFLG-ONp-MA-GFLG-Drug A) is reacted with poly(HPMA-co-MA-APMA-MA-GFLG-Drug B) to form the conjugate. 'GFLG' is disclosed as SEQ ID NO: 1.

Scheme 8.

Synthesis of poly(HPMA-co-MA-GFLG-ONp-MA-GFLG-Drug A)

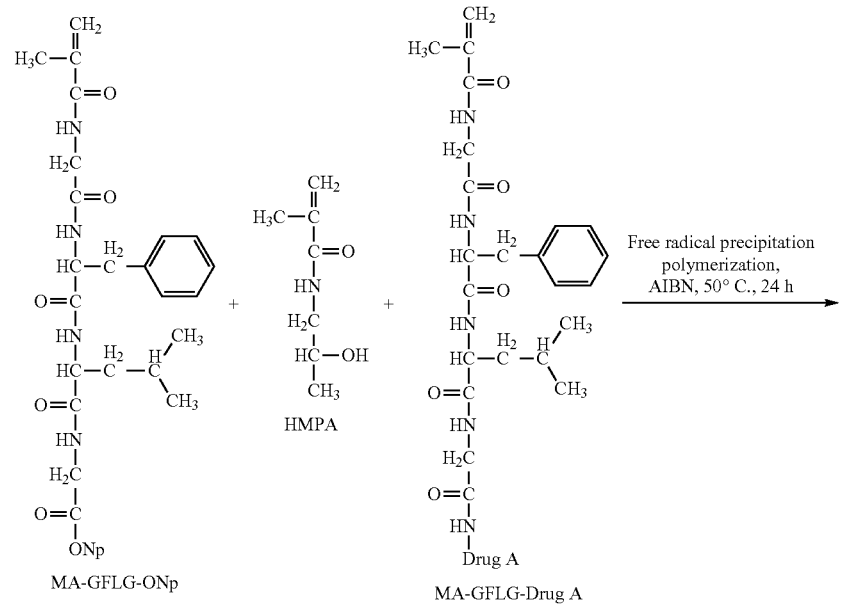

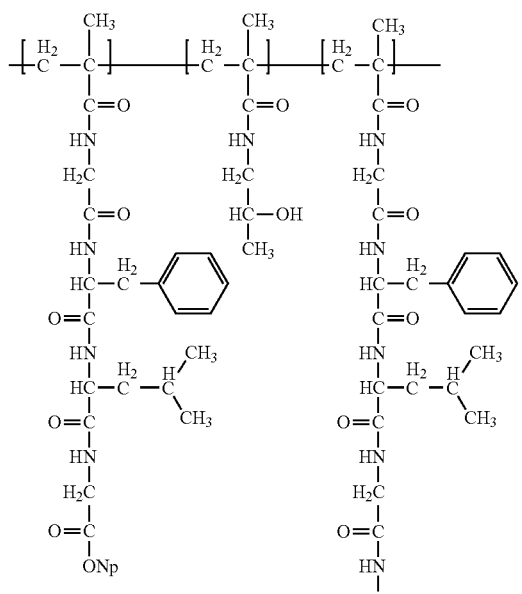

poly(HPMA-co-MA-GFLG-ONp-MA-GFLG-Drug A)

-continued
Synthesis of poly(HPMA-co-MA-APMA-MA-GFLG-Drug B)
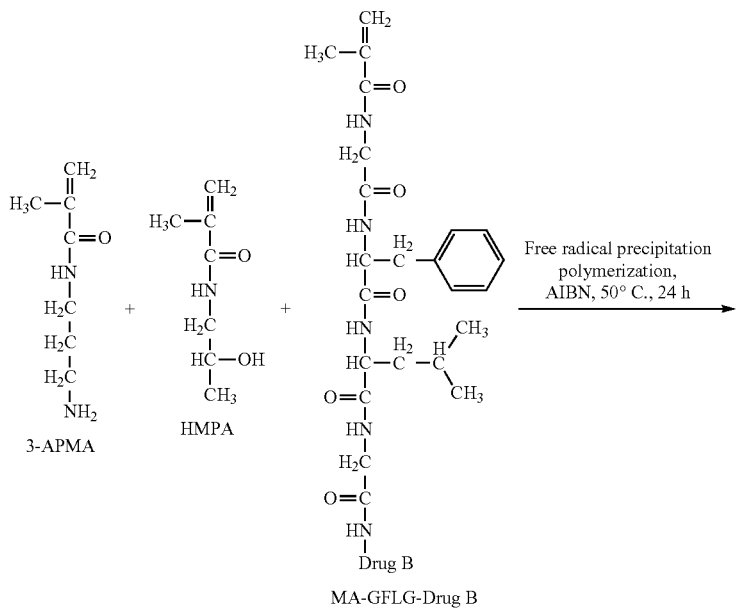
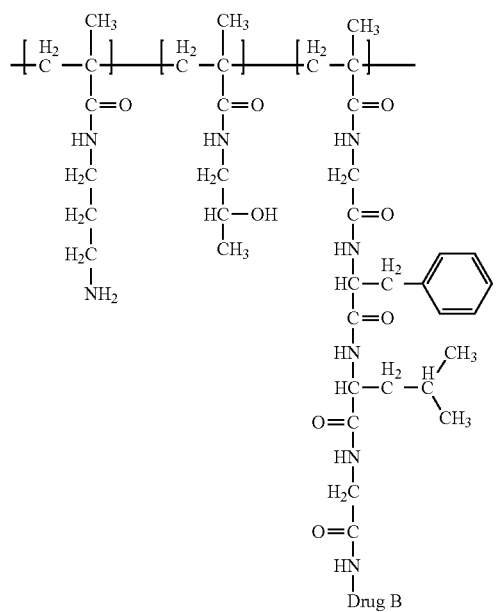
poly(HPMA-co-MA-APMA-MA-GFLG-Drug B)

Synthesis of polymer-Drug A/polymer-Drug B conjugate

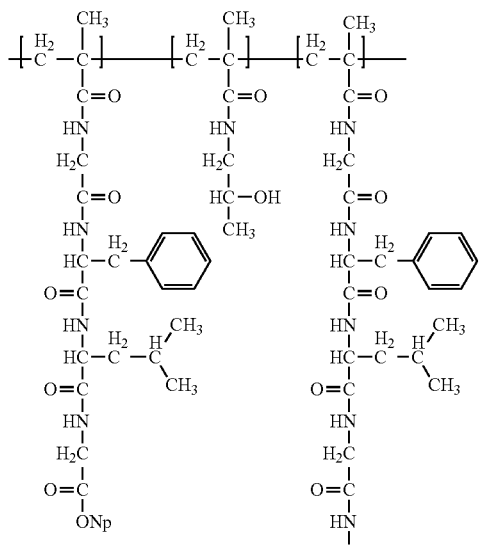

poly(HPMA-co-MA-GFLG-ONp-MA-GFLG-Drug A)

+

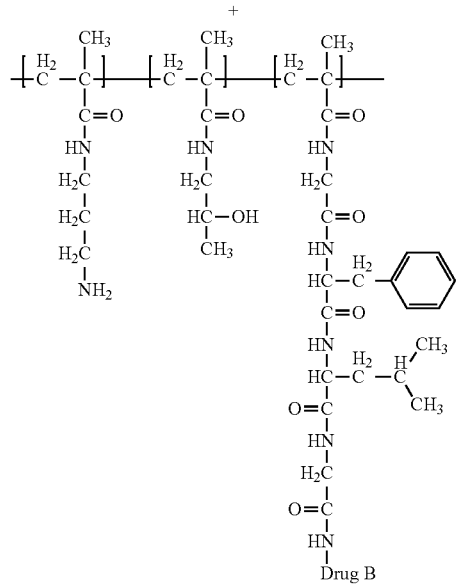

poly(HPMA-co-MA-APMA-MA-GFLG-Drug B)

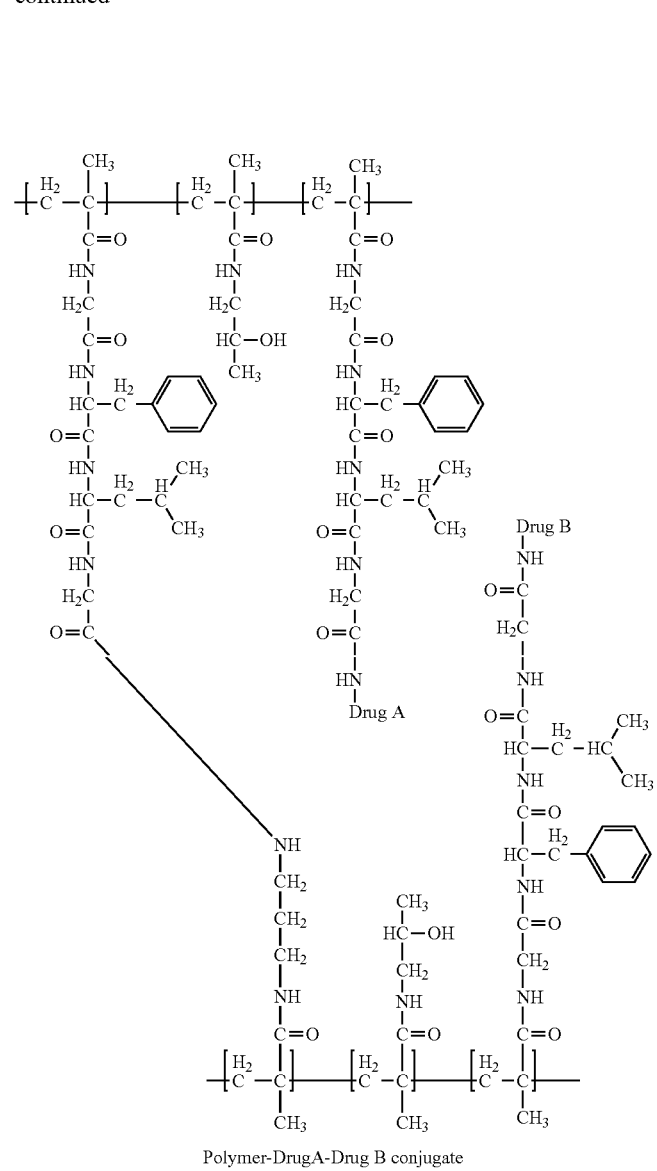

Polymer-DrugA-Drug B conjugate

Example 3

Biological Tests

Growth of Cancer Cell Lines

Cancer cell lines to determine the effect of polymer-drug conjugates were obtained from the following sources: Human MDA-MB-231 (breast), HCT116 (colon) and PANC-1 (pancreas), from the American Type Culture Collection (ATCC) (Manassas, Va.). UMRC2 (kidney) from United States National Cancer Institute (Bethesda, Md.). Cells were maintained in Dulbecco's modified Eagle's medium ("DMEM", Invitrogen) supplemented with 10% FBS, P/S and 10 mM HEPES. All cells were incubated at 37° C. under humidified 5% $CO_2$.

2) In Vitro Cell Proliferation Assay Against Human Tumor Cell Lines

The growth inhibition assay of polymer-drug conjugates against human cancer cell lines was performed using the Sulforhodamine B ("SRB") method (Skehan et al., J. National Cancer Institute, 82: 1107-1112 (1990)). Briefly, exponentially growing cancer cells were seeded into a 96-well plate at a density of $2-3 \times 10^3$ cells/well and treated with copolymer-drug conjugates the next day. Triplicate wells were used for each treatment. Water was used as a control. The cells were incubated with copolymer-drug conjugates for 96 hours at 37° C. in a humidified 5% $CO_2$ atmosphere. After 96-hour incubation, cells were fixed with 10% trichloroacetic acid ("TCA"), incubated for 1 hour at 4° C., and washed 3 times with tap water. Subsequently, cells were stained with 0.4% sulforhodamine B in 1% acetic acid for 30 minutes, washed 3 times with 1% acetic acid, and air-dried again. After 5 minutes agitation in 10 mM Tris solution, the absorbance of each well was measured at 530 nm using Benchmark Plus Microplate reader (Bio-Rad Laboratories, Hercules, Calif.). The absorbance value provides a direct measure of the number of live cells post-treatment with copolymer-drug conjugates.

To translate the $OD_{530}$ values into the number of live cells in each well, the $OD_{530}$ values were compared to those on standard $OD_{530}$—versus—cell number curves generated for each cell line. The percent survival was calculated using the formula:

% Survival=live cell number [test]/live cell number [control]×100

The $IC_{50}$ values were calculated by non-linear regression analysis.

TABLE 2

In-vitro cytotoxicity of docetaxel, pHPMA-GFLG-Docetaxel, p2-CPMA-GFLG-Docetaxel and p3-APMA-GFLG-Docetaxel against human cancer cell lines.

| Drugs | $IC_{50}$ (µM) of drug equivalent | | |
|---|---|---|---|
| | Caki-1 | MDA-MB-231 | HCT116 |
| Docetaxel | 0.0010 | 0.0015 | 0.00058 |
| pHPMA-GFLG-Docetaxel | 0.011 | 0.013 | 0.0056 |
| p2-CPMA-GFLG-Docetaxel | 0.013 | 0.013 | 0.0056 |
| p3-APMA-GFLG-Docetaxel | 0.013 | 0.017 | 0.0090 |

'GFLG' is disclosed as SEQ ID NO: 1.

Example 4

Ex Vivo Xenograft Study

In order to observe the inhibition of growth of tumor in an animal model, a nude mouse xenograft model were conducted utilizing polymer conjugated docetaxel or gemcitabine as described below.

HCT116 cell suspension ($2\times10^6$ cells in 0.1 ml of RPMI) were injected subcutaneously into the right flank of six-week-old male athymic mice (BALB/c nu/nu) on day 0. A sufficient number of mice were injected with HCT116 cell suspension so that tumors in a volume range as narrow as possible were selected for the trial on the day of treatment initiation. Animals with tumors in the proper size range were assigned to various treatment groups and were injected with phosphate buffered saline (PBS) only or with a polymer-drug conjugate of the invention. All study medications are given by intraperitoneal injections two times per week starting from day 5 and ending on day 32. To quantify tumor growth, three perpendicular diameters of the tumors are measured with calipers every 3-5 days, and the body weight of the mice is monitored for toxicity. The tumor volume is calculated using the formula: tumor volume $(mm^3)$=(width)×(length)×(height)×R/6. Results are shown in FIG. 1.

As described herein, all embodiments or subcombinations may be used in combination with all other embodiments or subcombinations, unless mutually exclusive.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A therapeutic composition comprising
a first polymer carrier; and
a first anticancer agent attached to the first polymer carrier, optionally through a linker,
wherein the first polymer carrier comprises
a) a first monomer selected from the group consisting of N-(2-carboxypropyl) methacrylamide (2-CPMA) and N-(3-carboxypropyl)methacrylamide (3-CPMA) and
b) optionally a second monomer; and
wherein the first anticancer agent is attached to the first monomer or
if the second monomer is present, the first anticancer agent is attached to the first monomer or the second monomer,
wherein the first polymer carrier comprises one or more monomer units, and
wherein each of the one or more monomer units is derivatized or underivatized.

2. The composition of claim 1 wherein the first polymer carrier further comprises a second monomer selected from the group consisting of N-(2-hydroxypropyl)methacrylamide, an acrylamide, a methacrylamide, an acrylate and a methacrylate.

3. The composition of claim 1 further comprising an additional anticancer agent attached to the first polymer carrier, optionally through a linker, wherein the additional anticancer agent is different than the first anticancer agent, and wherein the additional anticancer agent is attached to the first monomer or if a second monomer is present, the additional anticancer agent is attached to the first monomer or the second monomer.

4. The composition of claim 1, further comprising a targeting ligand attached to the first polymer carrier, optionally through a linker, where the targeting ligand is attached to the first monomer or if a second monomer is present, the targeting ligand is attached to the first monomer or the second monomer.

5. The composition of claim 4, wherein the targeting ligand is selected from the group consisting of RGDfK (arginine-glycine-aspartic acid-D-phenylalanine-lysine oligopeptide), EPPT1 (YCAREPPTRTFAYWG, that is, tyrosine-cysteine-alanine-arginine-glutamic acid-proline-proline-threonine-arginine-threonine-phenylalanine-alanine-tyrosine-tryptophan-glycineoligopeptide), and folate.

6. The composition of claim 1 further comprising a second polymer carrier and a second anticancer agent and/or a targeting ligand attached to the second polymer carrier, optionally through a linker.

7. The composition of claim 6, wherein the second polymer carrier is a polymer comprising a monomer selected from the group consisting of N-(2-hydroxypropyl)methacrylamide (HPMA), N-(2-carboxypropyl)methacrylamide (2-CPMA), N-(3-carboxypropyl)methacrylamide (3-CPMA), N-(3-aminopropyl)methacrylamide (3-APMA), and N-(2-aminopropyl)methacrylamide (2-APMA).

8. The composition of claim 6, wherein the first polymer carrier and the second polymer carrier are linked.

9. The composition of claim 1 wherein said first polymer carrier comprises (a) between about 5.0 and about 99.7 mol % of underivatized monomer units, (b) between about 0.2 and about 20.0 mol % of derivatized monomer units attached to an anticancer agent; and (c) between about 0 and about 94.8 mol % of derivatized monomer units attached to a targeting ligand.

10. The composition of claim 9 wherein said first polymer carrier comprises between about 0.1 and about 94.8 mol % of derivatized monomer units attached to the targeting ligand.

11. The composition of claim 1 having one or more linkers, wherein each of the one or more linkers is cleavable by lysosomal enzymes.

12. The composition of claim 11 wherein the linker is selected from the group consisting of oligopeptide sequences, oligosaccharide sequences, and oligonucleotide sequences comprising phosphodiester-ribose linkages.

13. The composition of claim 12, wherein the linker is an oligopeptide sequence selected from the group consisting of Gly-Gly, Gly-Phe-Gly, Gly-Phe-Phe, Gly-Leu-Gly, Gly-Val-Ala, Gly-Phe-Ala, Gly-Leu-Phe, Gly-Leu-Ala, Ala-Val-Ala, Gly-Phe-Leu-Gly (SEQ ID NO: 1), Gly-Phe-Phe-Leu (SEQ ID NO: 2), Gly-Leu-Leu-Gly (SEQ ID NO: 3), Gly-Phe-Tyr-Ala (SEQ ID NO: 4), Gly-Phe-Gly-Phe (SEQ ID NO: 5), Ala-Gly-Val-Phe (SEQ ID NO: 6), Gly-Phe-Phe-Gly (SEQ ID NO: 7), Gly-Phe-Leu-Gly-Phe (SEQ ID NO: 8), and Gly-Gly-Phe-Leu-Gly-Phe (SEQ ID NO: 9).

14. The composition of claim 13 wherein the oligopeptide sequence is Gly-Phe-Leu-Gly (SEQ ID NO: 1).

15. The composition of claim 1 wherein the first anticancer agent is selected from the group consisting of docetaxel, gemcitabine, and cisplatin.

16. The composition of claim 1, comprising at least two different anticancer agents, wherein at least one of the anticancer agents is selected from the group consisting of docetaxel, gemcitabine, and cisplatin.

17. The composition of claim 1, comprising a first linker and a second linker, wherein the second linker is an amino acid or a peptide.

18. The composition of claim 17, wherein the second linker is a peptide comprising Gly-Gly (GG).

19. The pharmaceutical composition comprising the composition of claim 1, in combination with a pharmaceutically acceptable carrier.

20. A method of treating a neoplastic disease comprising administering a therapeutically effective amount of a composition according to claim 1.

* * * * *